(12) United States Patent
Washington

(10) Patent No.: US 7,896,969 B2
(45) Date of Patent: Mar. 1, 2011

(54) METHODS AND SYSTEMS FOR ENHANCING THE EFFECTIVENESS OF CLEANING COMPOSITIONS

(75) Inventor: Les W. Washington, Dunwoody, GA (US)

(73) Assignee: Telechem Corporation, Atlanta, GA (US)

( * ) Notice: Subject to any disclaimer, the term of this patent is extended or adjusted under 35 U.S.C. 154(b) by 868 days.

(21) Appl. No.: 11/801,840

(22) Filed: May 12, 2007

(65) Prior Publication Data

US 2008/0280262 A1    Nov. 13, 2008

(51) Int. Cl.
*B08B 3/12*   (2006.01)
*C02F 1/48*   (2006.01)
(52) U.S. Cl. ............... 134/1; 134/42; 210/222; 210/223
(58) Field of Classification Search ................ 134/1, 42; 210/222, 223
See application file for complete search history.

(56) References Cited

U.S. PATENT DOCUMENTS

| 4,935,133 A | * | 6/1990 | Hirama | 210/222 |
| 6,093,287 A | * | 7/2000 | Sanderson | 204/157.15 |
| 6,164,332 A | | 12/2000 | Hatton | 137/827 |
| 6,602,411 B1 | | 8/2003 | Aida et al. | 210/222 |

OTHER PUBLICATIONS

Author Unknown, PiMag Magna Tote, Nikken Catalog, 1 page, Jan. 1, 2006.

* cited by examiner

*Primary Examiner* — Michael Barr
*Assistant Examiner* — Saeed T Chaudhry
(74) *Attorney, Agent, or Firm* — Roberta L. Hastrieter; Locke, Lord, Bissell & Liddell LLP

(57) ABSTRACT

The present invention provides inexpensive, safe and reliable methods and systems for enhancing the effectiveness of aqueous or non-aqueous, concentrated or non-concentrated, cleaning compositions, such as concentrated cleaning liquids, by "energizing" all, or a portion, of the water that is employed in the compositions, and/or in diluted aqueous or non-aqueous compositions, and/or of the compositions, and to enhanced cleaning compositions that are safe for use by human beings.

44 Claims, 46 Drawing Sheets
(41 of 46 Drawing Sheet(s) Filed in Color)

METHODS AND SYSTEMS FOR ENHANCING THE EFFECTIVENESS OF CLEANING COMPOSITIONS

BACKGROUND OF THE INVENTION

1. Field of the Invention

The present invention relates methods and systems for enhancing the effectiveness of cleaning compositions, such as concentrated cleaning liquids, by "energizing" all, or a portion, of the water that is employed in the compositions, or by diluting aqueous or non-aqueous concentrated cleaning compositions with "energized" water, and to cleaning compositions that have been enhanced in this manner.

2. Background

Conventional, commercial and other cleaning chemicals are often sold as concentrates and super concentrates that are diluted (generally according to recommendations of the manufacturer) prior to use to provide a proper solution strength for various applications, and for the best economy. Many of these chemicals are diluted 10:1 to 50:1 by hand (i.e. the chemical is measured out and added to a predetermined amount of water to achieve the recommended dilution). Disadvantageously, this method is typically not consistent. For example, five people who are all following the same instructions will generally end up with five different concentrations of chemical cleaner. This often results in an overuse of the cleaner, or in too strong of a cleaning product being applied to an object or surface during cleaning.

For many cleaning chemicals to be effective at higher dilution ratios, they must be formulated with very strong, sometimes dangerous, ingredients. Additionally, after use, these products must properly be discarded. If they are poured down a drain, they may fill water systems with harsh chemical products, and human beings that handle them may develop skin and eye burns.

Further, many aqueous and non-aqueous cleaning compositions, whether in the form of a liquid or other concentrate, or a non-concentrate, disadvantageously are very expensive. Such expense becomes even more significant when large areas, such as floors or walls, or numerous areas, are to be cleaned. Moreover, such cleaning compositions, which often include harsh chemicals, can cause health problems to humans and animals if vapors are inhaled, or if they become present on the skin or in the eyes.

It would be beneficial to provide inexpensive, safe and reliable methods and systems for enhancing the effectiveness of aqueous and/or non-aqueous cleaning compositions, such as concentrated cleaning liquids, as well as enhanced cleaning compositions.

U.S. Pat. No. 6,164,332 ("the 332 patent") discloses an apparatus that is designed to manufacture a relatively large quantity of living water for a home or business. The apparatus includes a plurality of ampuls (cylindrically-shaped containers) that are longitudinally aligned and connected together to enable the water delivered to the upper ampul to flow in a vortex pattern from the upper ampul to the lower ampul. Each ampul has a water dispensing unit which facilitates the flow of the water in a vortex pattern therein, and includes a longitudinally aligned neck with several pairs of magnets longitudinally aligned on the neck that create magnetic fields around the water as it flows in a vortex pattern through the neck. The apparatus is designed to be connected to a household water supply system, and includes a holding tank and control valve. In contrast with the methods and systems of the present invention, which do not require, and preferably do not have, a vortex flow or other type of a circulation system, which energize a substance or composition just prior to (including during) use, and which typically do not store an "energized" substance or composition, the '332 patent does not discuss cleaning, requires a vortex flow, does not "energize" water just prior to, or during, use and uses a holding system for collecting water that has left the lower ampul, thus, permitting the magnetic properties of the water to dissipate during storage.

U.S. Pat. No. 6,093,287 ("the 287 patent") discloses a magnetic processing treatment facility for subjecting a fluid flow to magnetic energy. The facility is integrated into an agricultural spray apparatus, and is stated to be effective in increasing the water solubility of chemical agents such as herbicides, pesticides, fertilizer, nutrient liquids and other liquids for agricultural use that are dispersed as a spray solution over an application area. The magnetically treated chemical solution is also stated to exhibit enhanced activity in terms of crop growth and pesticide and weed control. The treatment facility utilizes a magnetic core device having a resident permanent magnet for generating a magnetic field that is applied to a fluid volume passing through the device. In contrast with the methods and systems of the present invention, the '287 patent does not discuss cleaning or the use of any Gauss strength. (Permanent magnets are produced in a wide variety of Gauss strengths.) Further, the '287 patent describes the use of a storage system for the magnetically treated chemical solution, thereby permitting magnetic properties to dissipate therefrom, a pump and a spray dispersal unit. In contrast, the methods and systems of the present invention typically do not use a storage system, and do not require the use of a pump or a spray dispersal unit.

U.S. Pat. No. 6,602,411 ("the 411 patent") discloses a magnetic treating apparatus of water in which a combination of permanent magnets and an electric conductor is employed to increase the current generated in the apparatus. The apparatus is used for treating or conditioning potable water, industrial water, water passed through a building conduit, hot-springs, gardening water and recycled water in a factory. In contrast with the '411 patent, which requires the use of an electrical current, and the presence of at least two magnetic fields, with one being perpendicular to the other, in the methods and systems of the present invention, the "energized" composition has an ability to exhibit an enhanced activity in the absence of an electrical current, and with the presence of only one magnetic field. Also in contrast with the '411 patent, in the methods and systems of the invention, the N or S poles, or both, of the one or more magnets employed does not need to be aligned with, or positioned towards, or opposite to, the N or S poles, or both, of one or more other magnet. Further, the '411 patent does not discuss cleaning.

SUMMARY OF THE INVENTION

It has been surprisingly and unexpectedly determined that the effectiveness of aqueous and/or non-aqueous cleaning compositions, or aqueous and/or non-aqueous concentrated cleaning compositions that are to be diluted with water (or another aqueous composition), may be enhanced by energizing all (100%), or a portion (more than 0%, but less than 100%), of: (a) the water (or another aqueous composition) that is employed in, or to prepare, the aqueous cleaning compositions, or to dilute aqueous or non-aqueous cleaning compositions; and/or (b) the non-aqueous cleaning compositions, or ingredients thereof. The methods of the present invention advantageously provide inexpensive and reliable methods for enhancing the effectiveness of such cleaning compositions. The invention also provides enhanced cleaning compositions.

Both the methods and the compositions of the present invention are generally safe for use by human beings, and are often safer for use than other cleaning compositions because they are more effective for cleaning than the same or similar cleaning compositions that have not been "energized" and, thus, generally a smaller quantity of the cleaning compositions need to be used, decreasing an ability of a user to breath in harmful vapors, or to have the cleaning composition come into contact with the user's skin and/or eyes.

In one aspect, the present invention provides a method for increasing an activity or effectiveness of an aqueous or non-aqueous, concentrated or non-concentrated, cleaning composition (i.e., that is effective for cleaning one or more objects, or surfaces thereof) comprising "energizing" just prior to use (including during use, or at the point of use), at a temperature and pressure, and for a period of time, that are effective for such "energizing," a portion or all of the cleaning composition by positioning one or more magnets having a combined Gauss strength ranging from about 100 to about 10,000 Gauss in a manner in relation to the cleaning composition that one or more magnetic forces or magnetic fields are created on or over the cleaning composition, wherein the cleaning composition exhibits an enhanced activity or effectiveness for cleaning one or more objects, or surfaces thereof, in comparison with the same cleaning composition that has not been "energized," wherein the cleaning composition has an ability to exhibit the enhanced activity in the absence of an electrical current, and wherein if more than one magnet is employed, the magnets do not need to be positioned in any particular manner with respect to their polarities.

In another aspect, the present invention provides a method for increasing an activity or effectiveness of an aqueous or non-aqueous concentrated cleaning composition that is to (or will) be diluted with water (or with another aqueous composition) prior to use, and that is effective for cleaning one or more objects, or surfaces thereof, comprising:
  (a) "energizing" just prior to use (including during use, or at the point of use) at a temperature and pressure, and for a period of time, that are effective for such "energizing," a portion or all of the water (or other aqueous composition) that is employed to dilute the concentrated cleaning composition by positioning one or more magnets having a combined Gauss strength ranging from about 100 to about 10,000 Gauss in a manner in relation to the water (or other aqueous composition) that one or more magnetic forces or magnetic fields are created on or over the water (or other aqueous composition); and
  (b) diluting the concentrated cleaning composition with the "energized" water (or other aqueous composition);
wherein the concentrated cleaning composition becomes effective at a dilution ratio of water (or other aqueous composition) to concentrated cleaning composition ranging from about 1:1000 to about 1000:1;
wherein the diluted cleaning composition exhibits an enhanced activity or effectiveness for cleaning one or more objects, or surfaces thereof, in comparison with the same diluted cleaning composition that does not include "energized" water (or other aqueous composition);
wherein the diluted cleaning composition has an ability to exhibit the enhanced activity in the absence of an electrical current; and
wherein if more than one magnet is employed, the magnets do not need to be positioned in any particular manner with respect to their polarities.

In the above method, the aqueous or non-aqueous concentrated cleaning composition may, optionally, also be "energized." This may be performed in the same manner as is employed for the water (or another aqueous composition) that is used to dilute the concentrated cleaning composition. Alternatively, the aqueous or non-aqueous concentrated cleaning composition may be "energized," and the water (or other aqueous composition) may not be "energized." However, it is preferable that the water (or other aqueous composition) be "energized."

Thus, in another aspect, the invention provides a method for increasing an activity or effectiveness of an aqueous or non-aqueous concentrated cleaning composition that is to (or will) be diluted with water, or with another aqueous composition, prior to use comprising:
  (a) "energizing" just prior to use at a temperature and pressure, and for a period of time, that are effective for such "energizing," a portion or all of the concentrated cleaning composition by positioning one or more magnets having a combined Gauss strength ranging from about 100 to about 10,000 Gauss in a manner in relation to the concentrated cleaning composition that one or more magnetic forces or magnetic fields are created on or over the concentrated cleaning composition; and
  (b) diluting the concentrated cleaning composition with the water, or other aqueous composition, wherein the water or other aqueous composition is, optionally, also "energized" just prior to use at a temperature and pressure, and for a period of time, that are effective for such "energizing," a portion or all of the water, or other aqueous composition, by positioning one or more magnets having a combined Gauss strength ranging from about 100 to about 10,000 Gauss in a manner in relation to the water, or other aqueous composition, that one or more magnetic forces or magnetic fields are created on or over the water, or other aqueous composition;
wherein the concentrated cleaning composition becomes effective at a dilution ratio of water, or other aqueous composition, to concentrated cleaning composition ranging from about 1:1000 to about 1000:1;
wherein the diluted cleaning composition exhibits an enhanced activity or effectiveness for cleaning one or more objects or surfaces in comparison with the same diluted cleaning composition that does not include "energized" concentrated cleaning solution, water and/or other aqueous composition;
wherein the diluted cleaning composition has an ability to exhibit the enhanced activity in the absence of an electrical current; and
wherein if more than one magnet is employed, the magnets do not need to be positioned in any particular manner with respect to their polarities.

In yet another aspect, the present invention provides a method for removing some (more than 0% and less than 100%) or all (100%) of the calcium deposits, plaque deposits or stains from, or for whitening, one or more teeth of a human or animal subject comprising having the subject drink an amount of water (or other aqueous composition) that has been "energized" just prior to use (including during use, or at the point of use) by positioning one or more magnets having a combined Gauss strength ranging from about 100 to about 10,000 Gauss in a manner in relation to the water (or other aqueous composition) that one or more magnetic forces or magnetic fields are created on or over the water (or other aqueous composition) for a period of time that is effective for removing some or all of the calcium deposits, plaque deposits or stains from, or for whitening, the teeth of the subject, wherein the water may be "energized" without using an electrical current, and wherein if more than one magnet is employed, the magnets do not need to be positioned in any particular manner with respect to their polarities.

In still another aspect, the present invention provides a cleaning composition that is effective for cleaning one or more objects or surfaces comprising a cleaning composition that has been "energized" in one of the manners that are described above.

BRIEF DESCRIPTION OF THE DRAWINGS

The patent or application file contains at least one drawing and/or photograph that is executed in color. Copies of this patent or patent application publication with color drawing(s) and/or photograph(s) will be provided by the Office upon request and payment of the necessary fee.

DETAILED DESCRIPTION OF THE PREFERRED EMBODIMENTS

Figure 1:
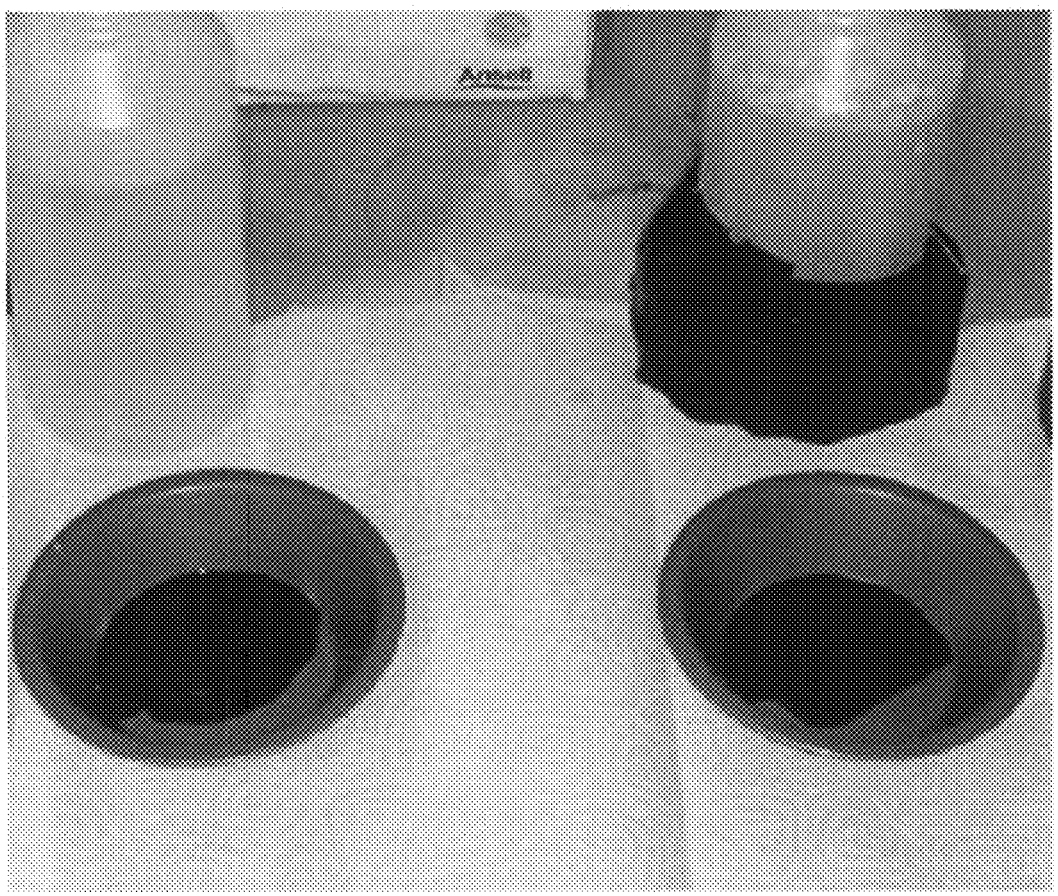
FIG. 1 is a photograph showing a perspective view of non-stick cake pan #1 (left side) and non-stick cake pan #2 (right side) after 3 mL of dirty motor oil was poured onto the upper surface of the bottom of each pan in Test No. 1 of Example 3, and prior to spaying either pan with an aqueous liquid.

The present invention may be understood more readily by reference to the following detailed description of the preferred embodiments of the invention, and to the examples included therein.

Definitions

For purposes of clarity, various terms and phrases used throughout this specification and the appended claims are defined in the manner set forth below. If a term or phrase used in this specification, or in the appended claims, is not defined below, or otherwise in this specification, the term or phrase should be given its ordinary meaning.

The terms "accelerate" and "accelerated" as used herein means to cause at least some increase in a rate or speed of an occurrence or event.

The phrase "active agent" as used herein means a chemical, agent, substance or material that is capable of producing or exhibiting an activity, such as cleaning, to at least some extent (i.e., it generally can readily participate in one or more chemical reactions). The activity of an active agent may vary widely, and may range, for example, from about 0.1% to about 100% (full activity), and preferably ranges from about 1% to about 100%, and still more preferably ranges from about 10% to about 100%, and still even more preferably ranges from about 25% to about 100%, and still even more preferably ranges from about 50% to about 100%, and still even more preferably ranges from about 75% to about 100%, and still even more preferably ranges from about 90% to about 100%.

The term "APC" as used herein means All Purpose Cleaner (forms A, B, C, D and/or E), which is commercially available from The Telechem Corporation (Atlanta, Ga.).

The phrase "aqueous composition" as used herein includes, for example, an aqueous liquid or solution, and means a composition that includes: (a) water ($H_2O$) in an amount ranging from about 0.97% to about 100% (pure water); and (b) optionally, one, or a plurality of, other components, including, but not limited to, atoms or ions of one or more elements, and/or chemical compounds. When one or more of such other components are present in an aqueous composition, the total of such components will generally be present in the aqueous composition in an about ranging from about 0.97% to about 99.03%. An aqueous composition may additionally include one, or a plurality of, other components or ingredients, as well, and includes aqueous liquids (liquids that contain water). It is preferable that an aqueous composition of the invention, or an aqueous composition that is employed in the methods of the invention, be in a form that can flow, such as a liquid, for example, water. The aqueous composition may be in any convenient or desired form, such as a solution, a dispersion, a suspension, an emulsion and the like, and should be safe for use if consumed by humans or animals. Those of ordinary skill in the art can readily determine whether or not an aqueous composition is safe for use by humans and/or animals.

The term "chemical" as used herein means a substance having a distinct molecular composition that is typically produced by, or used in, a chemical process.

The phrase "chemical process" as used herein means any process that may be determined by the atomic and molecular composition and structure of the substances involved.

The term "clean" as used herein means: (1) to partially (from greater than 0% to less than 100%) or fully (100%) free dirt, stains, debris, soil, grease, grime, oils, impurities, microorganisms and/or other unwanted matter or substances from an object, surface, material, structure or the like, such as a floor, wall, counter or window; or (2) to render an object, surface, material, structure or the like partially (from greater than 0% to less than 100%) or fully (100%) free of dirt, stains, debris, soil, oils, impurities, microorganisms and/or other unwanted matter or substances.

The terms "cleaning agent," "cleaning composition" and "cleaner" as used herein mean a substance, material or composition that can be used to clean or degrease, whether in a concentrated or non-concentrated form, such as soap, All Purpose Cleaner ("APC"), Simple Green® All Purpose Cleaner (Sunshine Makers, Inc., Huntington Harbour, Calif.), Simple Greeng Concentrated Cleaner (Sunshine Makers, Inc., Huntington Harbour, Calif.), 21 Guns Super Concentrate All Purpose Cleaner (The Telechem Corporation, Atlanta, Ga.), Pine-Sol® All Purpose Cleaner (The Clorox Company, Oakland, Calif.).

The term "composition" as used herein means the proportion and/or combination of elements, chemicals, compounds, components and/or ingredients, whether active, inactive, or both, and whether chemical and/or non-chemical, that are employed to form a substance or material that is liquid or semi-liquid, by, for example, combining, mixing, blending, or the like, such as a concentrated cleaning liquid (either prior to, or after, dilution with water).

The term "compound" as used herein means a substance that is composed of atoms or ions of two or more elements in a chemical combination. The constituents are united by bonds or valence forces. It is a homogeneous entity in which the elements have definite proportions by weight, and are represented by a chemical formula. A compound has characteristic properties that are different from those of its constituent elements. For example, water is generally a liquid that is formed by a chemical combination of two gases. It can be separated into hydrogen and oxygen by an electric current (electrolysis), and in certain reactions, it is split into its constituent ions (H and OH) by hydrolysis. It is not chemically changed by heat or cold.

The term "concentrate" as used herein means to increase the concentration of a mixture or solution (i.e. to increase an amount of one or more dissolved or other substances that are present in the mixture or solution), for example, by evaporating some or all of the solvent, such as water, that is present in the mixture or solution, or the product produced thereby.

The term "concentration" as used herein means the amount of a given substance in a stated unit of a mixture, solution or the like. Common methods for stating concentration are percent by weight, or by volume, normality, or weight per unit volume as grams per cubic centimeter or pounds per gallon. The concentration of an atom, ion or molecule in a solution may be indicated by square brackets, as $[Cl^-]$.

The phrase "diluent" as used herein means an ingredient, substance or material (usually inert), for example, water, that is used to reduce the concentration of a material (which is usually active), for example, a concentrated cleaning solution, which generally achieves a desirable and/or beneficial effect (i.e., it is used to dilute).

The term "dilute" as used herein means to make thinner and/or less concentrated, generally by adding a liquid, such as water.

The phrase "diluting substance" as used herein means any substance that has an ability to effectively dilute an aqueous or non-aqueous composition (i.e., to make it thinner and/or less concentrated), such as water (of any type).

The term "dispersion" as used herein means a two-phase system in which one phase consists of finely divided particles, which are often in the colloidal size range, distributed throughout a bulk substance, the particles being the disperse or internal phase and the bulk substance being the continuous or external phase. Under natural conditions, the distribution is typically not uniform. Under controlled conditions, however, the uniformity may be increased by an addition of one or more wetting or dispersing agents (surfactants), such as a fatty acid. An example of a liquid/liquid dispersion is an emulsion.

The term "effective" as used herein means having an ability to perform a particular function or purpose, whether partially (more than 0% and less than 100%) or fully (100%).

The term "energize" as used herein in connection with an aqueous or non-aqueous composition, such as water, means: (a) to give at least some magnetic, kinetic and/or other type of energy to such a composition that previously had no such energy; or (b) to enhance the magnetic, kinetic and/or other type of energy that an aqueous or non-aqueous composition may have previously had. Both results are preferably accomplished with the use of one or a plurality of magnets and/or electromagnets.

The term "emulsifier" as used herein means any substance or agent that aids in the formation of an emulsion, such as egg yolk, egg lecithin, soy lecithin and mono- and di-glycerides.

The term "emulsion" as used herein means a typically stable mixture of two or more immiscible liquids that are held in suspension by a small percentage of one or more emulsifiers (surface active agents). Emulsions are generally comprised of a continuous phase and a disperse phase. For example, in an oil-in-water emulsion, water is generally the continuous phase and oil is generally the disperse phase. In a water-in-oil emulsion, oil or free fat is generally the continuous phase and water droplets, or unbroken fat globules plus water droplets, are generally the disperse phase.

The term "energized" as used herein means having energy transferred to something, for example, to an aqueous or non-aqueous cleaning (or other) composition, or to one or more components or ingredients thereof. The amount of energy that is transferred is difficult to quantify.

The terms "enhance" and "enhances" as used herein in connection with an aqueous or non-aqueous composition of the invention mean that the composition functions in some manner that is improved (enhanced) in comparison with the same composition, but which does not include any "energized" substances or compositions, such as water, or the same quantity of such "energized" substances or compositions, such as in an accelerated manner, in a manner that accomplishes an improved result, or in a manner than accomplishes a result that would not otherwise occur. For example, a specified quantity of a concentrated cleaning composition that has a specified quantity of water added thereto (as a diluent), wherein a portion (more than 0%, but less than 100%) or all (100%) of the water is "energized," may be able to clean more deeply (i.e., get an object more clean) and/or more rapidly, in comparison with the same quantity of the same concentrated cleaning composition that has the same quantity of water added thereto, wherein none (0%) of the water is "energized," or wherein a smaller quantity of the water is "energized." As another example, a specified quantity of a concentrated cleaning composition that has a specified quantity of water added thereto, wherein a portion or all of the water is "energized," may be able to clean an object to a partial (more than 0%, but less than 100%) or full (100%) extent, whereas the same quantity of the same concentrated cleaning composition that has the same quantity of water added thereto, wherein none (0%) of the water is "energized," or wherein a smaller quantity of the water is "energized," does not have an ability to clean the same object at all.

The term "fat" as used herein means any of the various saturated and/or unsaturated (including monounsaturated and polyunsaturated), hydrogenated or unhydrogenated soft solid, semisolid and/or solid organic compounds that generally comprise the glyceride esters of fatty acids and associated phosphatides, sterols, alcohols, hydrocarbons, ketones and/or related compounds, components thereof and/or mixtures or other combinations thereof. Such components include, but are not limited to, fatty acids, glycerides (mono-, di- and tri-), ethyl and other esters of fatty acids, as well as components thereof, and combinations thereof. Fats occur widely in organic tissue, particularly in the subcutaneous connective tissue of animals (beef, poultry, pork, lamb, liver and the like), and in the seeds, nuts and fruits of plants. There is generally no chemical difference between fats and oils, with the only distinction being that fats are generally solid at room temperature and oils are generally liquid at room temperature.

The phrase "fatty acids" as used herein means carboxylic acids that generally are derived from, or contained in, an animal, vegetable or other fat or oil, whether saturated, unsaturated, monounsaturated, polyunsaturated, aromatic, essential, nonessential, in a cis or trans form, in the ethyl esters, mono-, di- or tri-glycerides, free fatty acids or other forms, and components and combinations of the foregoing. Most fats (including oils) contain a percentage of water.

The phrase "fatty acids" as used herein means carboxylic acids that generally are derived from, or contained in, an animal, vegetable or other fat or oil, whether saturated, unsaturated, monounsaturated, polyunsaturated, aromatic, essential, nonessential, in a cis or trans form, in the ethyl esters, mono-, di- or tri-glycerides, free fatty acids or other forms, and components and combinations of the foregoing. Fatty acids include, but are not limited to, the specific fatty acids identified below:

| Common Name | Number of Carbon Atoms | Number of Double Bonds |
|---|---|---|
| Butyric Acid | 4 | 0 |
| Caproic Acid | 6 | 0 |
| Caprylic Acid | 8 | 0 |
| Capric Acid | 10 | 0 |
| Lauric Acid | 12 | 0 |
| Myristic Acid | 14 | 0 |
| Palmitic Acid | 16 | 0 |
| Palmitoleic Acid | 16 | 1 |
| Stearic Acid | 18 | 0 |
| Oleic Acid | 18 | 1 |
| Linoleic Acid | 18 | 2 |
| Alpha-Linolenic Acid (ALA) | 18 | 3 |
| Gamma-Linolenic Acid (GLA) | 18 | 3 |
| Arachidic Acid | 20 | 0 |
| Gadoleic Acid | 20 | 1 |
| Arachidonic Acid (AA) | 20 | 4 |
| Eicosapentaenoic Acid (EPA) | 20 | 5 |
| Behenic Acid | 22 | 0 |
| Erucic Acid | 22 | 1 |
| Docosahexaenoic Acid | 22 | 6 |
| Lignoceric Acid | 24 | 0 |

Other fatty acids are known by those of skill in the art. Oils can be separated into their component fatty acids on a capillary column in a gas chromatograph, and the relative fatty acid contents measures. Additional information concerning fatty acids is readily available from the Fatty Acid Producer's Council (New York, N.Y.).

The phrase "force" as used herein means an influence that may cause an object to accelerate. It may be experienced as a lift, a push, or a pull, and has a magnitude and a direction. The actual acceleration of an object is determined by the vector sum of all forces acting on it (known as net force or resultant force). Force is a vector quantity that is defined as the rate of change of the momentum of the object that would be induced by that force acting alone. Since momentum is a vector, the force has a direction associated with it.

The phrase "human being" as used herein, unless otherwise stated, includes babies, infants, children, teenagers and/or adults.

The phrase "just prior to use" as used herein in connection with the "energizing" of a substance or composition, such as water, means that the substance or composition is preferably "energized" no longer than about 60 minutes, and more preferably no longer that about 35 minutes, and still more preferably no longer that about 28 minutes, and still more preferably no longer than about 21 minutes, and still more preferably no longer than about 15 minutes, and still more preferably no longer than about 10 minutes, and still more preferably no longer than about 7 minutes, and still more preferably no longer than about 5 minutes, and still more preferably no longer than about 3 minutes, and still more preferably no longer than about 1 minute, and still more preferably no longer than about 30 seconds, and still more preferably no longer than about 15 seconds, and still more preferably no longer than about 7 seconds, prior to use of the substance or composition for cleaning, with "point of use" being most preferable. See, for example, the table set forth below.

Preferable Time Prior to Use of Substance of Composition for Cleaning
Point of Use: 0 seconds
Seconds: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60
Minutes: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60

Through experimentation, it has been determined that the "energized" effectiveness of the substance or composition generally dissipates over a period of time. It has further been determined that, typically, liquid retains about 100% of an "energized" state up to about seven seconds after it has been "energized," about 70% of an "energized" state up to about 7 minutes after it has been "energized," about 35% of an "energized" state up to about 21 minutes after it has been "energized," about 14% of an "energized" state up to about 28 minutes after it has been "energized," and about 7% of an "energized" state up to about 35 minutes after it has been "energized."

The phrase "inactive agent" us used herein means a chemical, non-chemical or other agent, substance or material that is generally not capable of producing or exhibiting an activity (i.e., it does not readily participate in chemical reactions and is generally inert).

The term "lipid" as used herein means any of a group of organic compounds, including fats, oils, waxes, sterols, and triglycerides, that generally are insoluble in water, but are soluble in nonpolar organic solvents, are oily to the touch, and together with carbohydrates and proteins constitute the principal structural material of living cells.

The phrase "liquid" as used herein means a fluid or semi-fluid, the shape of which is generally determined by the container that it fills.

The term "magnetism" as used herein means one of the phenomena (generally an observable event) by which a material exerts some type of an attractive and/or repulsive force on one or more other objects and/or materials. Some well known materials that exhibit easily detectable magnetic properties are iron, some steels and the mineral lodestone.

The term "magnet" and "electromagnet" as used herein mean an object that is partially or fully surrounded by a magnetic field and/or that has the property, either natural or induced, of attracting iron, steel and/or other metal. All magnets typically have North-seeking (N) and South-seeking (S) poles. Generally, when magnets are placed near each other, opposite poles attract and like poles repel each other. There are many different types of magnets. For example, a "bar magnet" is a magnet in the form of a bar that has magnetic poles at each end. A "permanent magnet" is permanent in the sense that once it becomes magnetized, it generally retains a level of magnetism, such as the magnets that often hang onto refrigerator doors. Different types of permanent magnets may have different characteristics or properties concerning how easily they can be demagnetized, how strong they can be, how their strength varies with temperature, and so on, all of which can be determined by those of skill in the art. Four classes of "permanent" magnets include Neodymium Iron Boron (NdFeB or NIB), Samarium Cobalt (SmCo), Alnico and Ceramic or Ferrite. The table below provides some of the special characteristics of the four classes of "permanent" magnets.

| Material | Br | Hc | Bhmax | Tcoef of Br | Tmax | Tcurie |
|---|---|---|---|---|---|---|
| NdFeB | 12,800 | 12,300 | 40 | −0.12 | 150 | 310 |
| SmCo | 10,500 | 9,200 | 26 | −0.04 | 300 | 750 |
| Alnico | 12,500 | 640 | 5.5 | −0.02 | 540 | 860 |
| Ceramic or Ferrite | 3,900 | 3,200 | 3.5 | −0.20 | 300 | 460 |

"Br" is the measure of residual magnetic flux density in Gauss, which is the maximum flux the magnet is able to produce (1 Gauss is like 6.45 lines/sq in). "Hc" is the measure of the coercive magnetic field strength in Oersted, or the point at which the magnet becomes demagnetized by an external field (1 Oersted is like 2.02 ampere-turns/inch). "Bhmax" is a term of overall energy density. The higher the number, the more powerful the magnet. "Tcoef of Br" is the temperature coefficient of Br in terms of % per degree Centigrade. This describes how the magnetic flux changes with respect to temperature. −0.20 means that if the temperature increases by 100 degrees Centigrade, its magnetic flux will decrease by 20%. "Tmax" is the maximum temperature the magnet should be operated at. After the temperature drops below this value, it will generally still behave as it did before it reached that temperature (it is recoverable) (degrees Centigrade). "Tcurie" is the Curie temperature at which the magnet will become demagnetized. After the temperature drops below this value, it will generally not behave as it did before it reached that temperature. If the magnet is heated between Tmax and Tcurie, it will generally recover somewhat, but not fully (it is generally not recoverable) (degrees Centigrade). Both the Neodymium Iron Boron and the Samarium Cobalt magnets are generally known as rare earth magnets since their compounds come from the rare earth or Lanthanide series of the periodic table of the elements. As can be seen in the table, these are the strongest of the permanent magnets, and are more difficult to demagnetize. However, the Tmax for NdFeB is the lowest. Permanent magnets can be made or purchased in most any shape, size and strength imaginable. For example, they can be made into round bars, rectangular bars, horseshoes, rings or donuts, disks, rectangles, multi-fingered rings, and other custom or other shapes (circular, kidney shaped, square, rectangular, pentagonal, hexagonal and the like). Some magnets are cast into a mold and require grinding to achieve final dimensions. Others start as a powder, which is pressed into a mold or pressure bonded or sintered. For example, a small disc NIB magnet could be about 0.50" in diameter, and about 0.125" thick, or about 1" in diameter, and about 0.25" thick. As another example, a magnet in the shape of a marble could have about a 0.5" or a 1.0" diameter. As still another example, a magnet in the shape of a donut or ring could have an outer diameter of about 2.75", an inner diameter of about 1.125" and a thickness of 0.50". A "temporary magnet" is a magnet which generally acts like a permanent magnet when it is within a strong magnetic field, but generally loses its magnetism when the magnetic field disappears. Examples of temporary magnets include paperclips, nails and other soft iron items. An "electromagnet" is typically a tightly wound helical coil of wire, usually with an iron core, which acts like a permanent magnet when current is flowing in the wire. The strength and polarity of the magnetic field created by the electromagnet are generally adjustable by changing the magnitude of the current flowing through the wire and/or by changing the direction of the current flow.

The phrase "magnetic field" as used herein means a condition that is generally found in the region(s) around a magnet or an electric current, characterized by the existence of a detectable magnetic force, typically at every point in the region, and by the existence, of magnetic poles. A magnetic field is that part of an electromagnetic field that exerts a force on a moving charge. A magnetic field can be caused either by another moving charge (i.e., by an electric current) or by a changing electric field. The magnetic field is a vector quantity, and has SI units of telse, $1\ T=1\ kg \cdot s^{-1} \cdot C^{-1}$.

The phrase "magnetic force" as used herein means a fundamental force that generally arises from the movement of electrical charge. Maxwell's equations and the Biot-Savart law, both of which are known by those of skill in the art, describe the origin and behavior of the fields that govern these forces. Magnetism is generally seen whenever electrically charged particles are in motion. This can arise either from movement of electrons in an electric current, resulting in "electromagnetism," or from the quantum-mechanical spin and orbital motion of electrons. Electron spin is the dominant effect within atoms. The "orbital motion" of electrons around the nucleus is a secondary effect that slightly modifies the magnetic field created by spin. Keeping relativity in mind, and depending on the frame of reference, electromagnetic forces acting on an object generally partition differently into magnetic and electric fields.

The phrase "non-aqueous composition" as used herein includes, for example, a liquid or solution, and means a composition that includes water ($H_2O$) in an amount that is less than about 0.97%, such as 0%.

The term "object" as used herein means a thing, typically which can be seen and/or felt, including, but not limited to, a floor, ceiling, wall, window, screen, table, counter, cabinet, door, sink, toilet, bathtub, shelf, appliance (refrigerator, stove, oven, microwave oven, toaster, coffee maker, mixer, washer, dryer, television, radio, IPOD, VCR player, DVD player, stereo, lawn mower, leaf blower, grill and the like), office equipment (computer, printer, facsimile machine, monitor, paper shredder and the like), vehicle (car, truck, motorcycle and the like, including interior leather or other material), boat, wave runner, item of clothing, piece of furniture, lamp, carpet, drapery, curtain, item of jewelry, toy and/or one or more surfaces thereof, such as the upper surface of the floor, table or counter. The term "object" includes the interior and/or exterior parts or portions thereof.

The term "oil" as used herein means a fat that generally is viscous, liquid or liquefiable at room temperature, and may include a mixture and other combination of one or more oils and/or components of oils, such as fatty acids, glycerides and/or ethyl esters of fatty acids (or components thereof). Oils may be derived or obtained from animal, marine, algae, fungal, mineral, plant (including vegetables and plant seeds), fruit, nut, synthetic or other sources, and are generally composed largely of glycerides of the fatty acids, particularly oleic, palmitic, stearic and linolenic. Oils may be hydrogenated or non-hydrogenated, and saturated or unsaturated (including monounsaturated and polyunsaturated).

The phrase "plant seed oil" as used herein means an oil that is extracted, or otherwise obtained from, a seed of a plant, either directly or indirectly, particularly oily seeds, including one or more individual components thereof and mixtures thereof. Plant seed oils include, but are not limited to, Black Currant seed oil, Borage seed oil, safflower seed oil, sunflower seed oil, sesame seed oil, avocado seed oil, pumpkin seed oil, olive seed oil, coconut seed oil, rapeseed oil, flaxseed (linseed) oil, cottonseed oil, tung oil, meadowfoam seed oil, parsley seed oil, carrot seed oil, fennel fruit oil, parsnip seed oil, coriander seed oil, chervil seed oil, caraway plant oil and celery seed oil. Other plant seed oils are known by those of skill in the art.

The phrase "plant oil" as used herein means an oil that is extracted, or otherwise obtained from, a plant, either directly or indirectly, particularly oily plants, including one or more individual components thereof and mixtures thereof. Plant oils include, but are not limited to, Evening Primrose oil, Borage oil, safflower oil, sunflower oil, peanut oil, walnut oil, almond oil, avocado oil, olive oil, corn oil, soy oil, soybean oil, coconut oil, palm oil, palm kernel oil and castor oil. Other plant oils are known by those of skill in the art.

The term "plurality" as used herein means more than one, such as two, three, four, five, six, seven, eight, nine, ten, eleven, twelve, thirteen, fourteen, fifteen, sixteen, seventeen, eighteen, nineteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and fifty, two hundred, two hundred and fifty, three hundred, three hundred and fifty, four hundred, four hundred and fifty, five hundred, six hundred, seven hundred, eight hundred, nine hundred, one thousand and so forth.

The phrase "point of use" as used herein means that a substance or composition is being "energized" at about the same time, or at the same time, that it is being employed by a user for cleaning, for example, at the time a user is filling a mop bucket or spray bottle with the substance or composition.

The phrase "room temperature" as used herein means the temperature in a room, which generally ranges from about 15° C. to about 30° C. (from about 59° F. to about 86° F.), and more usually ranges from about 21° C. to about 23° C. (from about 70° F. to about 74° F). The "ambient temperature" of a room is "room temperature."

The phrase "safe for use" in connection with the compositions and methods of the present invention means that the compositions and methods, using reasonable quantities for reasonable periods of time (such as those quantities and periods of time described herein) do not cause, or present an unreasonable risk of harm, damage or injury to an average healthy human being that does not have, or suffer from, or have a history or having, or suffering from, allergies, diseases or illness. Preferably, such compositions and methods do not cause, or present, virtually any (or any) such risk.

The term "solution" as used herein means a uniformly dispersed mixture at the molecular or ionic level, of one or more substances (the solute) in one or more other substances (the solvent). These two parts of a solution are known as phases. Two common types of solutions are: (a) liquid/liquid, for example, alcohol in water; and (b) solid/liquid, for example, salt in water. Solutions that exhibit no change of internal energy on mixing and complete uniformity of cohesive forces are called ideal, and their behavior is described by Raoult's Law. Solutions are involved in most chemical reactions, refining and purification, industrial processing, and biological phenomena. The proportion of substances in a solution depends on their limits of solution. The solubility of one substance in another is the maximum amount that can be dissolved at a given temperature and pressure. A solution containing such a maximum is saturated. A state of supersaturation can be created, but such solutions are typically unstable and may precipitate spontaneously.

The term "solute" as used herein means one or more substances that are dissolved in another substance (the solvent), such as water. The solute is generally uniformly dispersed in the solvent in the form of either molecules, for example, sugar, or ions, for example, salt, with the resulting mixture comprising the solution.

The term "solvent" as used herein means a substance that is capable of dissolving another substance (solute), generally to form a uniformly dispersed mixture (solution), and at the molecular or ionic size level. Solvents are typically either polar (high dielectric constant) or non-polar (low dielectric constant). Water is the most common of all solvents, and is strongly polar (having a dielectric constant of 81), but hydrocarbon solvents are non-polar. Aromatic hydrocarbons have higher solvent power than aliphatics, such as alcohols. Other organic solvent groups include esters, ethers, ketones, amines and nitrated and chlorinated hydrocarbons. The chief uses of organic solvents are in the coating field (paints, varnishes and lacquers), industrial cleaners, printing inks, extractive processes and pharmaceuticals.

The phrases "surfactant" and "wetting agents" as used herein mean substances or agents that lower the surface tension (tendency of a liquid to reduce its exposed surface to the smallest possible area) of a liquid, generally allowing easier spreading, and/or the interfacial tension between two liquids. Surfactants are usually organic compounds that are amphipathic in that they contain both hydrophobic groups (their "tails") and hydrophilic groups (their "heads"). Therefore, they are typically sparingly soluble in both organic solvents and water. Surfactants generally reduce the surface tension of water by adsorbing at the air-water interface, and reduce the interfacial tension between oil and water by adsorbing at the liquid-liquid interface. Many surfactants can also assemble in the bulk solution into aggregates that are known as micelles.

The term "suspension" as used herein means an incorporation of one or more solid-state components into a semi-liquid or liquid vehicle, and includes colloidal and other types of suspensions. The suspension may be a uniform suspension (i.e. the components are uniformly present in a semi-liquid or liquid vehicle) or otherwise. If the particle sizes of the component particles are larger than colloidal dimensions (i.e., they are not small enough to pass through filter membranes), the component particles may have a tendency to precipitate (if they are heavier than the suspending medium) or agglomerate and rise to the surface (if they are lighter than the suspending medium). In both cases, the component particles may "settle out" of the suspension.

As used herein, the term "viscosity" means resistance to flow (of a fluid or semi-fluid). Viscosity can be measured using, for example, a commercially available viscometer.

The phrase "water" as used herein means $H_2O$, which may be in a liquid, solid and/or gaseous form, but is preferably in a liquid form that is clear, colorless, odorless and tasteless. Water has a freezing point of 0° C. (32° F.) and a boiling point of 100° C. (212° F). Water includes tap water, drinking water, bottled water, mineral water, natural spring water, natural artesian water, nursery water, purified water, distilled water, steam distilled water, deionized water, saline, sparkling water, carbonated water and/or other types of water that are known by those of skill in the art. All of the foregoing types of water may be obtained by, or purchased commercially from, sources that are known by those of skill in the art, such as PepsiCo, Inc. (Purchase, N.Y.—Aquafina), Coca-Cola Company (Atlanta, Ga.—Dasani), Deer Park Water Co. (Wilkes Barre, Pa.—Deer Park), Fiji Water (Los Angeles, Calif.—Fiji Water), or may be prepared by methods that are known in the art. Nursery water and steam distilled water are currently the most pure types of water that are sold commercially, and include no minerals, or a very small percentage of minerals. Dasani water is fortified with minerals. (Minerals provide water with an ability to have conductance (an ability to conduct or transmit electrical charge). Water that does not include minerals will generally not have this ability.)

The term "wax" as used herein means a fatty substance that generally is solid at room temperature and softens and melts when warmed. Generally, waxes are similar in composition to fats and oils, with the exception that they do not contain glycerides. Some waxes are hydrocarbons, and others are esters of fatty acids and alcohols. Examples of waxes include, but are not limited to, beeswax, lanolin, carnauba, candelilla, ozokerite, bayberry, sugar cane, paraffin, microcrystalline and sorbitol.

General Description and Utility

The present invention provides cost-effective, safe and reliable methods and systems for enhancing the effectiveness of aqueous and non-aqueous cleaning compositions, such as concentrated cleaning solutions, by energizing all, or a portion, of: (a) the water that is employed in the compositions; (b) the water (or other aqueous liquid or composition) that is employed to dilute the compositions (if any); and/or (c) the aqueous or non-aqueous compositions. Such methods can be employed by professionals, as well as by individuals, to enhance the effectiveness of aqueous and non-aqueous cleaning compositions. The present invention also provides enhanced aqueous and non-aqueous cleaning compositions.

The methods and systems of the present invention, for example, generally enhance the effectiveness of cleaning solutions or compositions for cleaning a wide variety of substances and/or materials, including, but not limited to, fats, lipids, fatty acids, oils, waxes and/or substances and/or materials that contain one or more fats, lipids, fatty acids, oils and/or waxes, for example, motor oil, cosmetics, salad dressings, and the like, from a wide variety of objects, surfaces, materials and the like.

One advantage of the methods and systems of the present invention is that no active electrical components, power sources, or electrical field quantities (i.e., current flows or voltage levels) are required or desired, making them self-contained and independently operative without susceptibility to electrical interference or disruption.

In the methods and systems of the invention, any flow or source of water, such as a line flow of a water supply leading to, or away from, a home or industrial and/or commercial building, or water flowing through a hose, that is "energized" provides water that has an enhanced performance in comparison with the same water that is not "energized." Further, the methods and systems do not require a vortex flow or other circulation of water and/or compositions, and preferably do not include any holding and/or storage systems and/or apparatuses, such as a storage tank or a container, for collecting and/or storing the water.

In the methods and systems of the invention, the water (and/or aqueous and/or non-aqueous compositions) is preferably "energized" just prior to use, for example, as it is being used, and most preferably at the point of use, thus, eliminating problems that are associated with the storage of the water (and/or compositions), such as a dissipation of magnetic properties from "energized" water (and/or compositions) during storage thereof over time, rendering the water (and/or compositions) less effective. Further, the methods and systems provide "energized" water (and/or compositions) on demand as they are being used, require no specific application method, such as a spray dispersal unit, and do not require the use of a pump, or current from an electrical conductor. Rather, the methods and systems of the invention have an ability to operate off of household or city water pressure, requiring no pump or electrical current.

Water

While any type of water may be employed in the methods and systems of the present invention, the most preferred type of water for use is steamed distilled water.

The amount of water that may be used in the methods and systems of the invention may vary widely. Generally, the amount of water that is employed ranges from about 0.01 to about 100 weight percent (pure water) of the total weight of final aqueous or non-aqueous compositions, and preferably ranges from about 52 to about 100 weight percent, and more preferably ranges from about 90 to about 100 weight percent, with about 99 weight percent being most preferred. Generally, no matter what percentage of water is contained in, or added to, an aqueous or non-aqueous composition, the water that is present in the composition and/or water that is employed to dilute the composition, can be "energized," thereby rendering the composition and/or one or more components therein, such as an active agent, more effective.

"Energizing" of Compositions

In the methods and systems of the present invention, any or all of the following may be "energized" in the manner described herein in order to enhance the effectiveness of aqueous or non-aqueous, concentrated or non-concentrated, cleaning compositions: (a) a non-concentrated aqueous or non-aqueous cleaning composition (i.e., one that is to be used without dilution); (b) water (or another aqueous or non-aqueous composition) that is employed to dilute a concentrated aqueous or non-aqueous cleaning composition (i.e., one that is to be diluted prior to use); and/or (c) a concentrated aqueous or non-aqueous cleaning composition that is to be diluted with water (or with another aqueous or non-aqueous composition) prior to use. However, it is preferred that water and/or aqueous compositions be "energized" in accordance with these methods and systems.

Any type and shape of magnets can be used to "energize" aqueous and non-aqueous compositions in accordance with the methods and systems of the invention. However, preferred magnet types for such use are permanent magnets, preferred magnet shapes are bar, disc and/or cube shapes, and preferred magnet sizes range from about $\frac{1}{4} \times \frac{1}{2} \times \frac{1}{2}$ inch to about $2 \times 6 \times 4$ inches, and more preferably range from about $\frac{1}{2} \times 1 \times 1$ inch to about $\frac{3}{4} \times 2 \times 1\frac{1}{2}$ inch. The physical size of the magnets is not as important as the strength of the magnets.

While it is possible to use only one magnet to "energize" aqueous and/or non-aqueous compositions in accordance with the methods and systems of the invention, it is preferable to use more than one magnet (two, three, four, five, six, seven, eight, nine, ten, eleven, twelve, thirteen, fourteen, fifteen, sixteen, seventeen, eighteen, nineteen, twenty and so forth), and it is most preferable to use two magnets. Testing that has been performed with different numbers of magnets show that the use of one magnet may not be as effective as the use of more than one magnet. Advantageously, the magnets need not be used in pairs, and need not be placed in any particular direction (north, south, east, west, horizontal, perpendicular and/or otherwise) with respect to one another, or with respect to the composition(s) being energized. Further, they do not need to have alternating polarities. However, it is preferred that one or more magnetic fields and/or magnetic forces be produced across at least some portion of the compositions by the use of at least two magnets. More than one magnetic field and/or magnetic force may be created, for example, by using more than two magnets. Each magnet employed will create a magnetic force and/or magnetic field. Thus, the more magnets that are used, the more magnetic forces and/or magnetic fields will be created, and the more area that will generally be covered by the magnetic fields.

The magnetic field and/or magnetic force that is created in and/or over the composition causes the composition to become "energized." For example, to "energize" a bottle of Dasani water, one magnet could be placed in a central location on one side of the bottle, and a second magnet could be placed in the same or similar location on the opposite side of the bottle, thus causing a magnet field and/or magnetic force to go across the bottle of water (between the two magnets).

The positioning of the one or more magnets is generally not critical, and the magnets can generally be positioned in any desired manner on, or near to, a composition, as long as at least one magnetic force and/or magnetic field is created on or over the aqueous or non-aqueous composition (generally by emanating from the magnets through a plastic, rubber, cardboard, paper, metal or other barrier, such as the plastic container of a water bottle or a PVC or copper pipe). For example, in a line of water in a hose leading away from a residence, the water in the line should flow through the magnetic force and/or magnetic field. Those of ordinary skill in the art can readily determine how close each of the one or more magnets must be to the aqueous or nonaqueous composition in order to create such a magnetic force and/or magnetic field.

Preferably, the one or more magnets used should be no farther than about ⅓ inch away from the side of a barrier, such as a PVC water pipe, or the container of a bottle of water, in which the water (or other aqueous composition or non-aqueous composition) is present or flowing, and more preferably should be in direct contact with such barrier (i.e. connected directly to the barrier). For example, a bottle of Dasani (or other) water could have one magnet placed underneath the bottom of the bottle (that part of the bottle that can rest upon a surface), and a second magnet could be positioned just above the top of the bottle (that part of the bottle upon which a bottle cap can rest). As an alternative, four magnets could be present on the bottle (two on either side of the bottle, one underneath the bottle, and one on top of the bottle).

Unless a magnet is sealed within some type of a waterproof barrier, and does not restrict the flow of liquid, it is preferable that the one or more magnets that are employed in the methods and systems of the invention not be in direct contact with the water (or other aqueous or non-aqueous solution), but rather be separated therefrom by some type of a barrier, such as a PVC pipe. Otherwise, over time, the magnets may become corroded and, thus, less effective for producing a magnetic force or magnetic field, and/or the water may become contaminated with one or more impurities (and become less effective).

The magnets may be positioned adjacent to the aqueous or non-aqueous composition, such as dilution water, and/or to a container containing the same, in any convenient or desired manner, for example, by placing a sleeve that contains one or more magnets snugly around a bottle of water, as is described in Example 1, or by using removable or non-removable electrical tape, clear packing/mailing tape, or other tape, Velcro® material, clips, metal, plastic or material fasteners, and the like to tape or affix the one or more magnets onto an associated barrier or container. For large volumes of water, such as water within pipes that flow to a residence, it is preferable to have a flow through method in which the unenergized composition passes through the magnetic force and/or magnetic field and exits the device as an "energized" composition.

Figure 39:
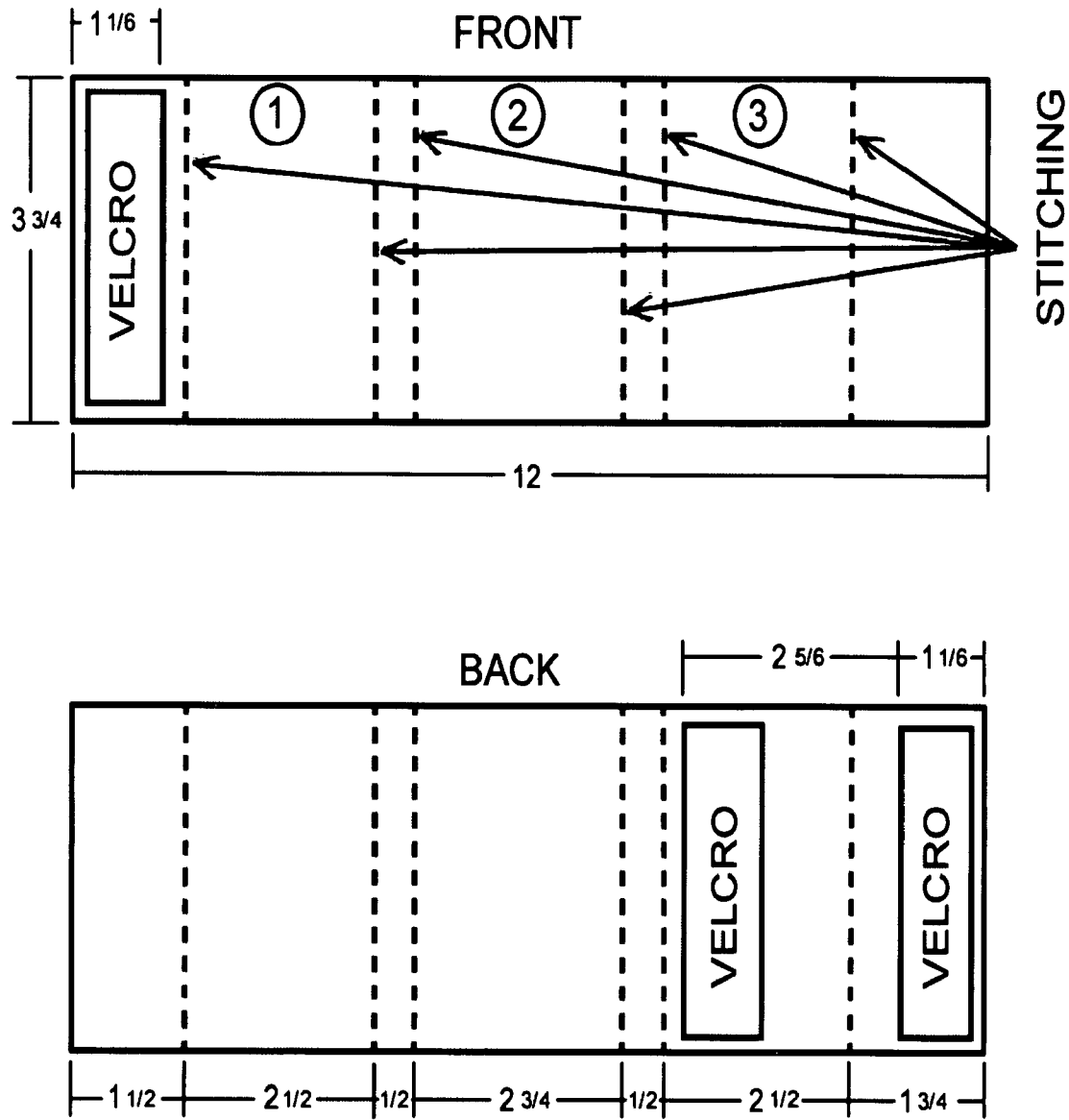
FIG. 39 is an illustration of the sleeve that is described in Example 1 in connection with bottle #3.

A sleeve (holder for one or more magnets) that is preferably used for "energizing" aqueous and/or non-aqueous compositions is illustrated in FIG. 39. This particular sleeve can hold from about 1 to about 3 magnets for energizing a variety of different liquids in a variety of different containers. The sleeve includes Velcro® material to fasten in a conventional manner easily around a pipe that ranges from about ¾ to about 3 inches in diameter, water (or other) bottles of various sizes, trigger sprayers, aerosol cans and the like. It has three pockets that can hold, for example, one or more magnets that are about 2½ inches in length×about 2 inches in width×about ⅝ of an inch in height in multiple configurations. It was made from a piece of fabric that is about 12 inches in length and about 7½ inches in width, and that is folded in half (lengthwise). It is stitched on both ends, and its pockets are made by stitching six times across the folded piece as shown. Velcro® material was added as indicated to allow the sleeve to be fastened around different size objects and/or containers, such as bottles of water, PCV pipe, spray bottles and/or spray cans. For example, two magnets could be placed into pockets 1 and 3, and the outermost Velcro® strips could secure the holder around a water bottle or spray can. For small water (and other) pipes, pockets 1 and 2 would preferably be used. All pockets (1, 2, and 3) would preferably be used at the same time around large diameter pipes. The size and shape of the sleeve, the size, shape and number of pockets, and the materials used to produce the sleeve can be varied widely using conventional materials and methods, as would be known by those of skill in the art.

For the "energizing" of lines of water (or other compositions), such as lines of water running to, or away from, a house or industrial or commercial building, it has been determined that the use of at least two magnets located on opposite sides of the lines (one at a designated location on one side of the lines, and the other at the same location on the opposite side of the lines), and placed in contact with the lines in a fasten position (by fastening them to the lines), are the most effective. Preferably, two magnets having a gauss strength ranging from about 1500 to about 3500, for from about ⅝ inch to about 1 ½ inch water lines, are employed. For larger diameter lines, it is preferably to employ additional magnets, such as four magnets, six magnets, eight magnets, and so forth, so that the entire circumferences of the lines are partially or fully (100%) covered. However, generally, two magnets (only) that are mounted on the lines in this manner will produce the desired results described herein.

The total (combined) Gauss strength of the magnetic force and/or magnetic field that is produced by the one or more magnets (in combination) to "energize" the aqueous or non-aqueous compositions according to the methods and systems of the present invention generally ranges from about 100 to about 10,000 Gauss, and preferably ranges from about 200 to about 9,000 Gauss, and more preferably ranges from about 500 to about 8,000 Gauss, and still more preferably ranges from about 800 to about 7,000 Gauss, and still more preferably ranges from about 1,000 to about 6,000 Gauss, and still more preferably ranges from about 1,500 to about 5,500 Gauss, and still more preferably ranges from about 2,000 to about 5,000 Gauss, and still more preferably ranges from about 3,000 to about 4,000 Gauss, and still more preferably ranges from about 3,500 to about 4,000 Gauss, and is most preferably about 3,500 Gauss. For example, if two magnets are employed, both of the magnets could produce a magnetic field and/or magnetic force having a Gauss strength of about 2,000 Gauss, or one of the magnets could produce a magnetic field and/or magnetic force having a Gauss strength of about 1,000 Gauss, and the other magnet could produce a magnetic field and/or magnetic force having a Gauss strength of about 3,000 Gauss, both resulting in a magnetic field and/or magnetic force having a total Gauss strength of about 4,000 Gauss. As another example, if four magnets are employed, each magnet could produce a magnetic field and/or magnetic force having a Gauss strength of about 1,000 Gauss, resulting in a total Gauss strength of about 4,000 Gauss. If eight magnets are employed, each magnet could produce a magnetic field and/or magnetic force having a Gauss strength of about 500 Gauss, resulting in a total Gauss strength of about 4,000 Gauss. It is preferable, but not critical, that each magnet that is employed produce a magnetic field and/or magnetic force having the same Gauss strength. Within the above ranges, it is most desirable to have as strong of a magnetic force and/or magnetic field as possible acting upon the aqueous and/or non-aqueous composition, wherein the magnetic force and/or magnetic field is positioned as close as possible to the composition, such as water flowing through a strong magnetic force and/or magnetic field emanating from one or more magnets that are attached directly to a pipe through which the water flows. Generally, the higher the number of magnets that are employed, and/or the higher the Gauss strength of the magnets that are employed, to "energize" a particular composition, the more "energized" a composition will become.

The compositions may be "energized" at a temperature generally ranging from about 37° F. to about 705° F. while at a pressure ranging from about 0 to about 3,206 psi, and preferably ranging from about 60° F. to about 212° F. while at a pressure ranging from about 40 to about 70 psi, with a temperature ranging form about 75° F. to about 180° F. and a pressure of about 45 to 65 psi being most preferred. Those of ordinary skill in the art may readily determine an optimal pressure to use in connection with a particular temperature.

The one or more magnets may be used to "energize" an aqueous and/or non-aqueous composition in accordance with the methods and systems of the invention for a period of time that is effective for energizing the compositions. From the numerous experiments that have been conducted by the inventors, it appears that the "energizing" of the compositions occurs virtually instantaneously when the compositions are exposed to the magnetic field in the manner described herein (i.e. that the molecules of the compositions become almost immediately changed). However, there appears to be a correlation between the strength of the magnet(s) that are used to "energize" the compositions and the amount of time that is required to "energize" the compositions. The stronger the Gauss strength of the magnet(s) is, the less time that is typically required to "energize" the compositions. While it appears not to be necessary, such a period of time may extend from a period of immediate exposure, 0.1 seconds, to any other desired period of time, such as 1 second, 5 seconds, 10 seconds, 30 seconds, 1 minute, 2 minutes, 3 minutes, 5 minutes, 7 minutes, 10 minutes, 15 minutes, 20 minutes, 25 minutes, 30 minutes, 45 minutes, 1 hour, 2 hours, 1 day and so forth. Preferably, such an amount of time ranges from about 0.1 seconds to about 1 minute, and more preferably ranges from about 0.1 seconds to about 1 second.

The "energizing" of the aqueous and/or non-aqueous compositions appears to physically change the structure and/or arrangement of the molecules that are present in the compositions (i.e., water molecules, and other molecules, if present). Water that is present in aqueous compositions appears to become "wetter," thereby rendering the aqueous compositions generally more effective for cleaning and/or teeth whitening. The ability of the water to penetrate porous materials, and to bring solvents into solution (dissolve them), becomes enhanced. If the aqueous composition is steam distilled water, which is extremely pure, it should contain nothing but water ($H_2O$), oxygen (O) and carbon dioxide (CO).

The more "energized" an aqueous and/or non-aqueous composition becomes, the more effective that the composition will generally be for cleaning or teeth whitening purposes, and the less of the composition will generally be required to perform a particular task, such as cleaning dirty motor oil off of a non-stick cake pan. The "energizing" of the aqueous and/or non-aqueous composition, thus, very advantageously can significantly reduce the cost of performing such tasks (because a smaller quantity of an aqueous and/or non-aqueous composition that has been "energized" can generally produce the same results as a larger quantity of an aqueous and/or non-aqueous composition that has not been "energized").

Further, because those molecules that may present in an aqueous and/or non-aqueous composition that is not 100% water also generally become different (in structure, arrangement and/or kinetic energy level), the portion of the composition that is not water generally also becomes more effective and, thus, less of the composition can be used to accomplish the same task or purpose. Such composition can also be diluted with water, or with another aqueous composition, which is generally less expensive than the other components, to a greater extent, if desired, without losing an effectiveness of the other components. For example, if a bottle of a commercial liquid cleaning substance that is not "energized" contains only about 10% water, as a result of the cost of the chemicals in the cleaning substance, such a bottle would likely cost more to produce than a bottle of the same cleaning substance that contains about 50% water (i.e. one that is more dilute and, thus, that contains more water, which is less costly than the chemicals, and a smaller quantity of the other components). If the first commercial cleaning substance (containing about 10% water) is "energized," less of the cleaning substance will typically be required to perform the same job and, thus, the cleaning substance can be diluted with more water to make the cost to produce the bottle of cleaning substance substantially cheaper.

Through the performance of numerous experiments, the inventors have found that any active agent having an ability to clean, such as a chemical cleaning agent, that is diluted with water that has been "energized" will retain its effect as an active agent at dilution ratios of water to active agent generally ranging from about 1:1000 to about 1000:1, including, for example, about 1:10 to about 10:1, about 1:25 to about 25:1, about 1:50 to about 50:1, about 1:75 to about 75:1, about 1:100 to about 100:1, and about 1:500 to about 500:1. A product having a dilution ratio of about 1000:1 is almost 100% water and, thus, would be much less expensive to use and produce than the same product that has a dilution ratio of about 1:1000, which contains almost no water. Although the product having a dilution ratio of about 1000:1 would be very inexpensive to manufacture, it would typically still be effective for achieving the purpose of the active agent, such as cleaning, if the water has been "energized" (because the active agent would still be effective). However, the same product having the same dilution ratio, but employing water that is not "energized," would not likely be effective for achieving the purpose of the active agent, such as cleaning (because the active agent would not be effective).

The above dilution ratios are a very significant improvement over recommended dilution ratios that are currently being used for various cleaning agents. For example, the manufacturer of Simple Green® All-Purpose Cleaner (Sunshine Makers, Inc.) recommends on its web site www.simplegreen.com the following dilution ratios of Simple Green® to water:

Heavy Cleaning
1:1 up to 1:10 Dilution (Example: 1 oz. Simple Green® to 1 cup water)
Light Cleaning
1:30 Dilution (Example: 1 oz. Simple Green® to 4 cups water)
Stains
1:1 Dilution (Example: 1 oz. Simple Green® to 1 oz. water)

As another example, Pine-Sol® All Purpose Cleaner recommends on its current label that, for "tough jobs," to use the cleaning agent full strength (a 100:0 dilution ratio), and for general cleaning and floors, ¼ cup (2 fluid ounces) per gallon (128 fluid ounces) of water (a 1:64 dilution ratio). Generally, the more dilute an aqueous solution (or other aqueous composition) is, the lower the cost will be per gallon for a particular application, such as cleaning. Thus, it is extremely advantageous to have an active agent be effective at a large dilution.

Figure 40:
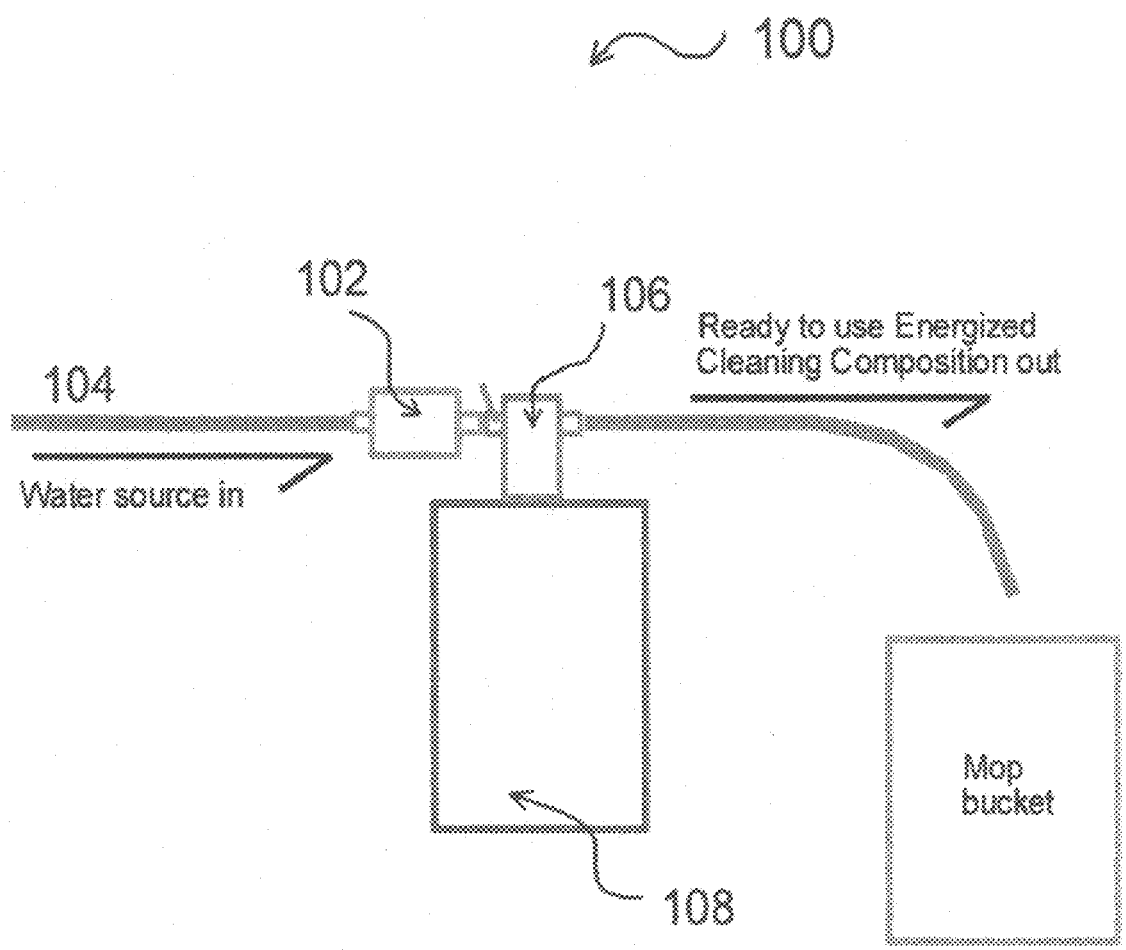
FIG. 40 is an illustration of an "energizing" pre-treatment apparatus that is preferred for use in "energizing" a supply of source water, and that is attached to a 5-gallon square pail containing cleaning composition.

The length of time that the aqueous compositions remain "energized" (at all, or to a certain percentage) is not clear. It is possible that some dissipation of the energy may occur from the aqueous and/or non-aqueous composition over time, with more dissipation occurring over longer periods of time. Thus, although it is not necessary, because the benefits achieved by "energizing" a composition will likely dissipate over time, it is preferable to "energize" the aqueous and/or non-aqueous composition itself, and/or part or all of the water (or other aqueous. or non-aqueous composition) that is used to prepare and/or dilute the composition, at the "point of use" (i.e., preferably immediately prior to, or while, the final product is being used to clean, or as soon as possible prior to such use, and at the location of use, given the time and dynamics that may be involved in any composition flow and/or mixing). This may be performed manually, for example, in the manner described hereinabove for the bottles of Dasani water, or via one or more apparatuses, such as the apparatus that is shown in FIG. 40, which is preferred for use, and which is commercially available from Hydro Systems (Cincinnati, Ohio). It is preferred to "energize" any aqueous and/or non-aqueous composition that is to be employed in the final cleaning product as close in time as possible to the actual use of the compositions in cleaning operations, such as just prior to use, and more preferably imimediately prior to use, and most preferably at the point of use.

The apparatus 100 that is shown in FIG. 40 (without the water "energizing" component) is commercially available from Hydro Systems (Cincinnati, Ohio), and has been used as a dilution device. With respect to the methods of the present invention, the apparatus 100 has been modified to include a water "energizing" component, and advantageously may be employed by an end user "on site" (at the location of use) to "energize" source (or other) water (or other aqueous or non-aqueous composition) just prior to, or while, it is being automatically. mixed with a predetermined amount of a concentrated (or other) cleaning composition, such as Ultra Green Ultra Concentrate chemical (The Telechem Corp. Atlanta, Ga.). The final cleaning product dispensed from this apparatus 100 (generally into a mop bucket) is typically a "ready-to-use" diluted cleaning composition that may be used by the user for cleaning a wide variety of objects, surfaces and/or materials. The apparatus 100 does not require any type of electricity to operate, and uses water pressure to siphon fluid.

The apparatus 100 generally includes a water "energizing" (pretreatment) component 102 that may be connected via a hose adaptor located at its proximate end with a source of supply water 104, which supplies water to the apparatus 100, and that may be connected at its distal end via threads with a water proportioning unit 106. The apparatus 100 may be permanently or removably attached to a container 108 containing a concentrated cleaning composition to be diluted.

Figure 41:
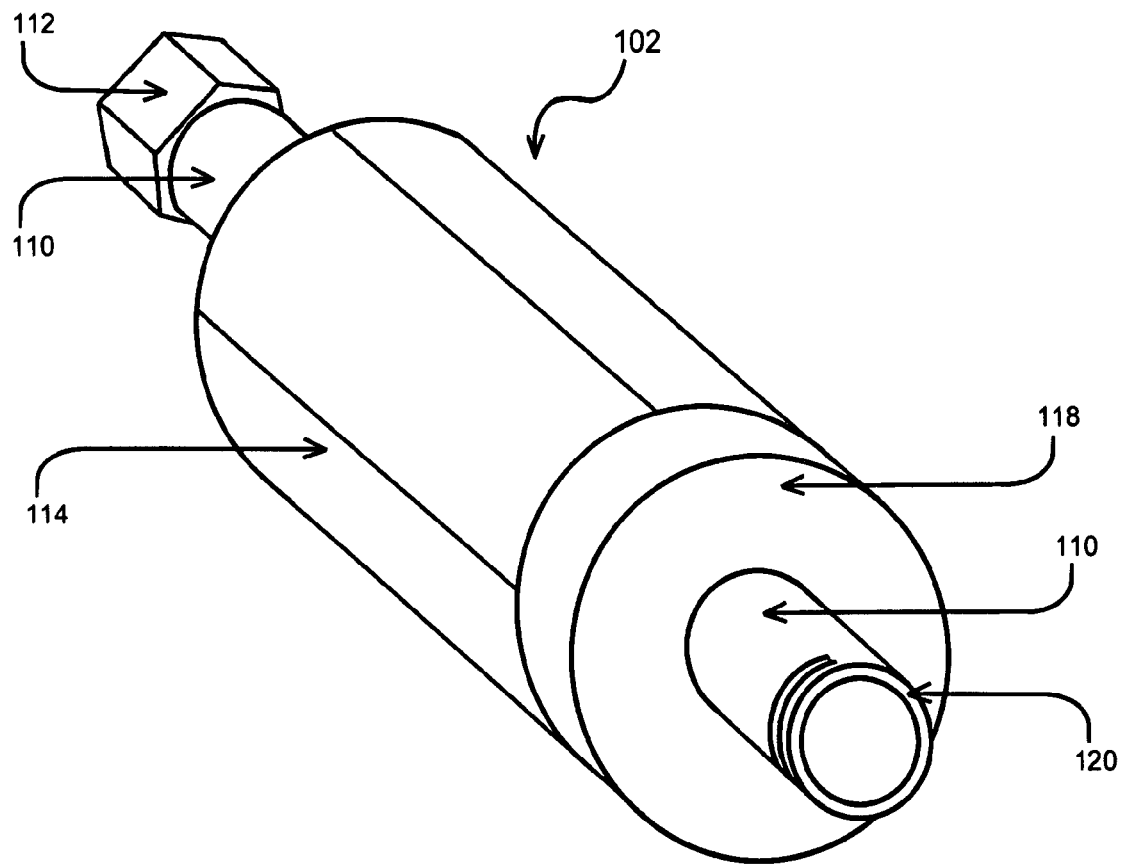
FIG. 41 is a perspective view of the water "energizing" component of the "energizing" pre-treatment apparatus that is shown in FIG. 40.
Figure 42:
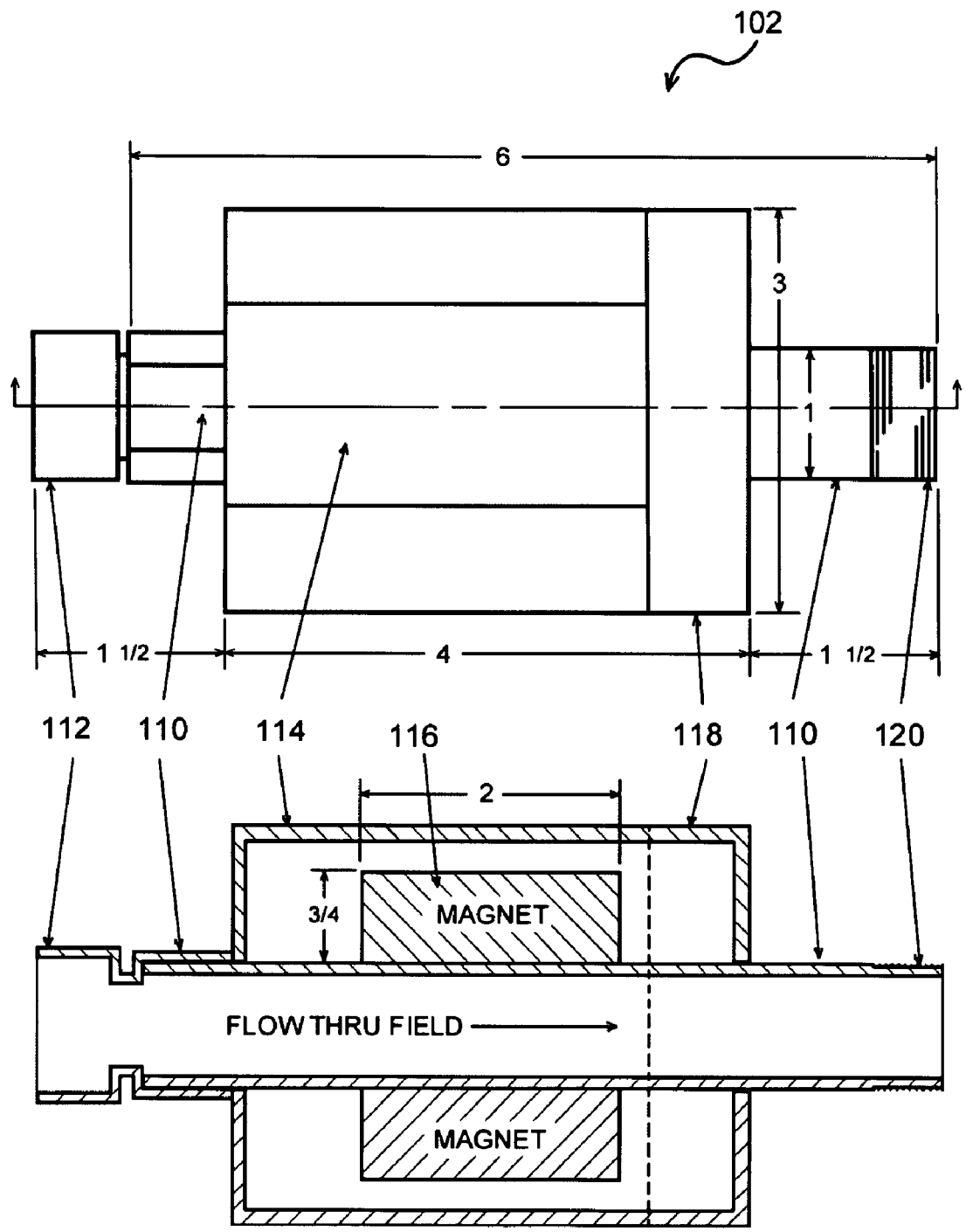
FIG. 42 is a sectional view of the water "energizing" component of the "energizing" pre-treatment apparatus that is shown in FIG. 40.

The water "energizing" component 102, which is illustrated in FIGS. 41 and 42, preferably includes at one end a six inch male threaded inlet pipe 110 made of PVC, which extends the length of the water "energizing" component 102, and a ¾ inch female hose adaptor 112 for connection with a supply of source water, such as a garden (or other) hose. A central portion thereof preferably includes a plastic casing 114 that encases a pair of permanent (or other) magnets 116 on opposite sides of the plastic casing 114, each of which has a Gauss strength of about 3500, which produce a strong magnetic field through which source water is passed, aligning and "energizing" the water molecules. At its distal end, the water "energizing" component 102 includes a cap 118 attached to the end of the plastic casing 114 and a threaded exit end 120 of the inlet pipe 110, which attaches to the water proportioning unit 106. The apparatus 100 is designed to be attached to a normal water supply, such as the distal end of a garden (or other) hose, water line or the like, that has its proximate end connected with a faucet, so that the water source may be turned "on" and "off" manually by a user. When the apparatus 100 or water proportioning unit 112 is not being used, the water source is preferably turned "off." The apparatus 100 permits the concentrated cleaning composition to be diluted with "energized" water in the ratios described herein for cleaning of all types of objects, surfaces and/or materials.

The container 108 that houses a concentrated (or partially diluted) cleaning composition to be diluted may be any conventional or suitable container, such as a 5-gallon stackable square pail, which preferably permits the apparatus 100 to be attached thereto. This container 108 functions to contain the concentrated cleaning composition before it is diluted or used, and can simply be replaced with another such container 108 when the concentrated cleaning composition becomes completely expended (i.e., when the container 108 becomes empty). Potentially, a set of two 5-gallon stacked square containers 108 could produce up to about 10,000 gallons of final cleaning product, which should be effective for cleaning and safe for humans and the environment.

Figure 43:
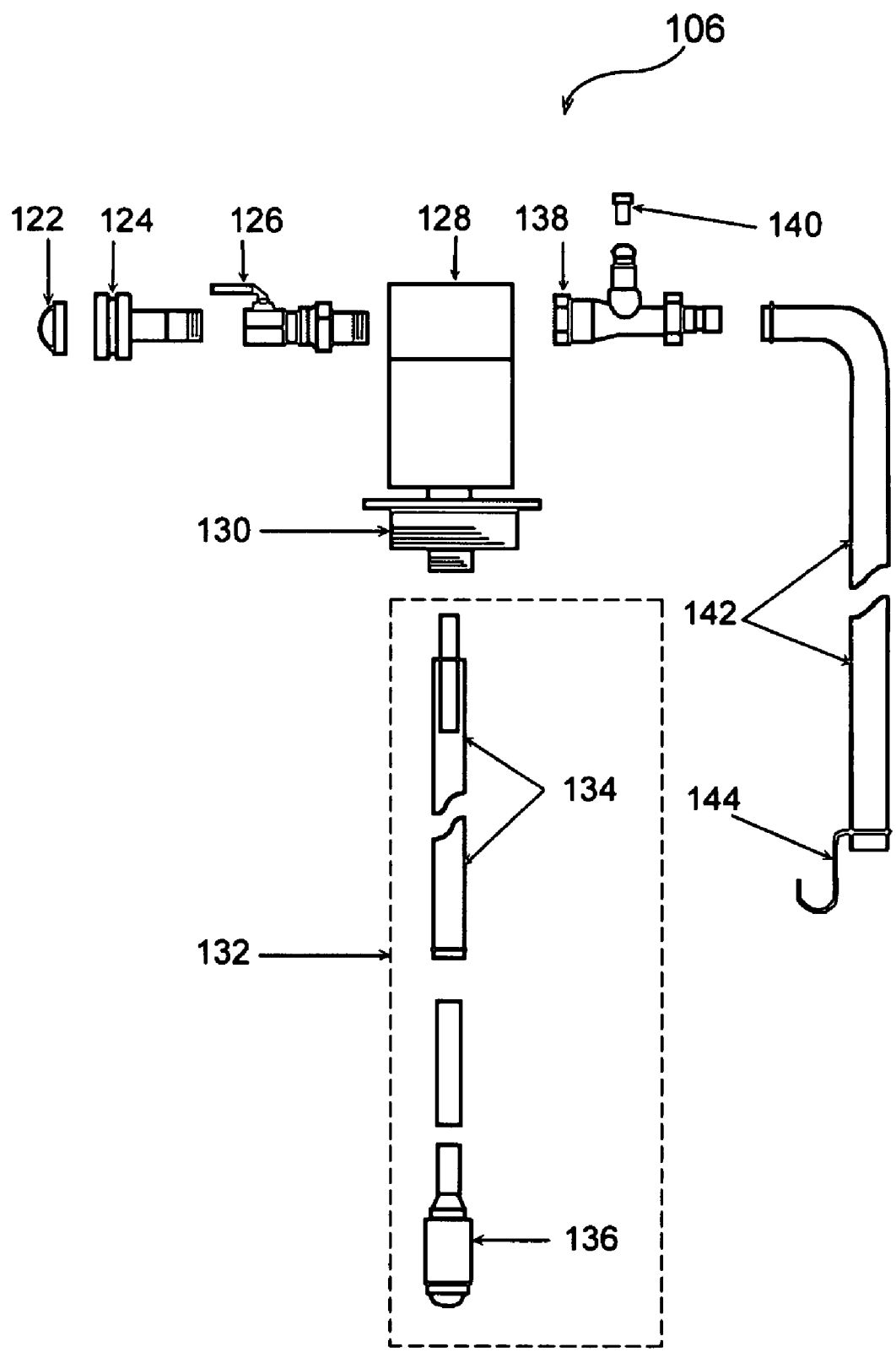
FIG. 43 is an illustration of the water proportioning unit of the "energizing" pre-treatment apparatus that is shown in FIG. 40.
Figure 44:
FIG. 44 is a photograph of a sleeve for holding one or more magnets that is affixed to both a water bottle and a spray can.
Figure 45:
FIG. 45 is a photograph of a sleeve for holding one or more magnets that is affixed to both a hose coupling and a spray bottle. (Another hose with a matching receiving end would typically attach to that fitting.)
Figure 46:
FIG. 46 is a photograph of a sleeve for holding one or more magnets that is affixed to both a rubber garden hose and a pipe including a valve, which is a copper water supply line.

The water proportioning unit 106 is shown in FIG. 43 (with components thereof being positioned in the manner in which they are positioned in the unit 106, but with space between many of the components). This unit 106 preferably includes a screen and washer 122, which function to seal a hose connection of a hose that preferably extends from the distal end of the water "energizing" component 102 to the proximate end of the water proportioning unit 106, a water inlet connection 124 that permits "energized" water to flow from the water "energizing" component 102 to the water proportioning unit 106. A control valve 126 that is preferably included within the water proportioning unit 106 may be positioned in an "open" position (by moving a lever in a counterclockwise direction) when a user wants to dispense concentrated cleaning composition from the system 106, or in a "closed" position (by moving a lever in a clockwise direction) when this is not so desired. The water proportioning unit 106 also includes a hydro body 128 that uses water pressure to draw and dilute the chemical, having a threaded end 130 that can screw onto the cap that is present on a 5-gallon (or other) drum or container containing concentrated cleaning composition. A central portion of the threaded end 130 of the hydro body 128, is hollow, and connects with a suction assembly 132 that is inserted into the drum, and that suctions concentrated cleaning composition from the drum into the hydro body 128. The suction assembly 132 includes a pickup hose 134 that is inserted into the drum, and suctions concentrated cleaning composition from the drum into the hydro body 128, and that is connected with a foot valve 136. The foot valve 136 filters debris that may be, or become, present in the drum, so that such debris does not become present in the final product (diluted cleaning composition), and in corporate a check valve to maintain the fluid in the pickup hose 134 in a ready to dispense position. On the side of the other end of the hydro body 128 is screwed an eductor 138 that draws solution via a siphoning action created by the water flow, thus mixing concentrated cleaning composition with water, and that includes a metering tip 140 that controls the dilution ratio of the concentrated cleaning composition and water by controlling the quantity of concentrated cleaning composition that is drawn up and mixed with water by varying the size orifice the tip contains. A predetermined amount of a concentrated (or other) cleaning composition can be automatically mixed with a predetermined amount of water, thereby producing a diluted cleaning composition having a desired dilution ratio. Any type of dilutions can be set on the apparatus 100, for example, dilutions of water to cleaning composition of from about 50:1 up to about 1024:1. The mixed (final) and "ready-to-use" cleaning product then flows from the eductor 138 through a filler hose 142 to an empty (or other) mop bucket, or other container used by an end user to hold the diluted cleaning composition. A J-hook 144 is preferably used to hang the filler hose 142 on either the hydro body 128 of the side of the drum. (The filler hose 142 should not be placed in to the drum.)

The various components of the apparatuses 100 may be purchased commercially, or manufactured using a wide variety of different materials, such as PVC, metal and/or other suitable materials that are known by those of skill in the art. However, such materials should have good mechanical characteristics and an ability to resist oxidation, corrosion and stress. The apparatus 100, and the components thereof, may be produced in any desired or convenient size and/or shape capable of producing desired results, and may be scaled in size to properly fit a wide variety of industrial or other applications.

The flow of the source water that travels through the apparatus 100, or that is used in other types of "point of use" apparatuses or systems, preferably ranges from about 1.5 to about 100 gallons per minute, and more preferably ranges from about 2 to about 7 gallons per minute, and most preferably ranges from about 3.5 to about 4 gallons per minute.

The Ultra Green and other formulations are generally safe for the environment, and can be washed down any drain or sewer. (It is recommended, however, first to have this type of a disposal approved by a regional water department.) The concentrated cleaning composition is diluted using the "energized" source water, and the diluted cleaning solution is then dispensed through the device 100 in a manner that the diluted cleaning solution can be used for cleaning almost immediately after being produced.

The combination of the water pretreatment unit 102 with the water proportioning unit 106 (including a calculated preset dilution dispenser) and the cleaning composition advantageously provides a user with continual, consistent performance and maintains environmental conformity. No adjustment of the diluted composition by the user is generally necessary because of this three-part system. This apparatus 100 can remove virtually all of the disadvantages that are associated with dilution error, which can result in application difficulties, thereby affecting the overall friendliness of a product in regard to environmental impact, and allows usage to remain consistent and effective while ensuring a proper dilution.

The apparatus 100, and the present invention generally, provide a method of pre-treating the source water by "energizing" and aligning water molecules for better wetting and penetration of the diluted cleaning composition as it is being used, thus, eliminating any need for the storage of either treated water or diluted cleaning solution. This feature, combined with an accurate and automated dilution by the water proportioning unit 106, provide a unique way to deliver the proper mix of cleaning chemicals to the user in an "on demand" situation.

Other conventional (or other) dispensing units may also be used in the methods of the invention. Alternatively, dilutions of concentrated cleaning compositions may be performed manually (i.e. by hand without the use of a dispensing unit). However, the latter method is less preferred because the dilutions obtained are generally less accurate and inconsistent. Also, prior to using any dilution apparatus, the end user could make a first manual dilution of a desired type. For example, with respect to the apparatus 100, rather than placing 5 gallons of undiluted concentrated cleaning solution in a 5-gallon container, the user could first manually mix 2.5 gallons of water with 2.5 gallons of concentrated cleaning solution in the 5-gallon container, providing an initial dilution ratio of water to concentrated cleaning composition of about 1:1. The user could then use the apparatus 100 in the manner described above to make other dilution ratios of the cleaning composition and water. Potentially, this could result in from about 320 to about 5,000 gallons of "ready-to-use" cleaning solution from just one 5-gallon pail, and up to about 10,000 gallons from each set of two 5-gallon pails, and so forth.

The table below shows final dilution ratios of Ultra Green Ultra Concentrate chemical cleaner that can be obtained using the apparatus 100 that is described above.

| Final Dilutions of Ultra Green Ultra Concentrate Chemical Cleaner (Water to Chemical Cleaner) | | |
| --- | --- | --- |
| Dilution | | Yields* |
| 2 five gallon pails × 64:1 | yields | 2 × 5 × 64 or 640 gallons |
| 2 five gallon pails × 104:1 | yields | 2 × 5 × 104 or 1,040 gallons |
| 2 five gallon pails × 176:1 | yields | 2 × 5 × 176 or 1,760 gallons |
| 2 five gallon pails × 240:1 | yields | 2 × 5 × 240 or 2,400 gallons |
| 2 five gallon pails × 1024:1 | yields | 2 × 5 × 1024 or 10,240 gallons |

This column shows how yield was arrived at in gallons, for example, 2×5×64=640 gallons.

Production of Magnets

The magnets that are used in the methods of the invention, or to produce the compositions of the invention, may be purchased commercially from sources that are known by those of skill in the art, such as from Dura Magnets, Inc. (Sylvanie, Ohio), K & J Magnetics, Inc. (Jamison, Pa.), ALL Magnetics, Inc. (Anaheim, Calif.) or The Electrodyne Company, Inc. (Batavia, Ohio), or may be made.

Steps that may be used to produce a magnet, such as a Neodymium Iron Boron magnet=$Nd_2Fe_{14}B$ or $Nd_{15}Fe_{77}B_8$, are set forth below.

1. Make an alloy of iron, boron and neodymium. It generally takes about 0.014 pounds of boron and 0.369 pounds of neodymium for every pound of iron to make an alloy of $Nd_2Fe_{14}B$. The alloy will have to be heated above 1538° C. to make it melt.
2. Allow the alloy to cool.
3. Grind the alloy into a fine powder using conventional grinding equipment.
4. Using a mold, compress the powder into a desired shape of a desired size. For example, if the shape of a disc is desired, pour the powder into a mold that has a disk shape, but that is also deeper than the thickness of the final part. Then, compress the powder with hundreds of pounds of pressure to compact the powder into a solid disk. Heat is often used to help fuse the particles together, and is called a sintered magnet. Sometimes a glue is used to help keep it all together, and is considered to be a bonded magnet. Grinding equipment may be used to achieve precise final dimensions for the magnet.
5. In order to improve the corrosion resistance of the magnet, the disk may be coated or plated with a thin film of nickel, or a film of gold, zinc or epoxy. Nickel does not oxidize in the manner that iron does, so it generally works well for magnets that will be touched.
6. Magnetize the magnet. (Prior to this step, the powder and the magnet are generally not magnetized. The magnet would likely be attracted, and stick, to a magnet, but would not likely be able to pick up a paper clip all by itself.) The magnet may be magnetized by methods that are known by those of skill in the art, such as by placing it into a magnetizing fixture that has a coil of wire through which a very large pulse of current is passed for a very short period of time. It takes only about one thousandth of a second to magnetize the magnet.

Aqueous Compositions

The aqueous compositions that are produced by the methods of the invention include at least about 1 weight percent water of the total weight of the aqueous compositions.

The aqueous (and other) compositions may be in the form of a mixture, a solution, a dispersion, a suspension, an emulsion or microemulsions (water-in-oil, oil-in-water, oil-in-water-in-oil, water-in-oil-in-water, and the like), or in any other suitable form, which may readily be determined by those of ordinary skill in the art.

Methods, equipment, techniques and ingredients that are generally employed in the preparation of the aqueous and non-aqueous compositions of the invention, and to carry out the methods of the invention, are well known by those of skill in the art, and may be obtained from sources that are known by those of skill in the art.

Below are some examples of different types of compositions, or uses therefore, that could be employed with the methods and systems of the invention, all of which involve some aspect of a cleaning process (to increase efficiency, run time and/or life of unit).

1. Any use of water for heating, steam generation, cooling, drinking, washing, manufacturing, felt washing and wire washing in paper and/or pulp manufacturing;
2. Paper manufacturing;
3. Oil production;
4. Medicines having a solution of about 3% or greater of water (to make them more effective);
5. Potable drinking water for health and for cleaning the blood stream of cholesterol and calicumization type deposits buildup within the recalculating system of the human body. (It may be possible to prevent many clogged arteries if enough "energized" water is drank daily, for example, 1000 to 4000 ml per day. The other 3 days, one could also drink "energized" a healthy mineral water such as Fiji Water or Dasani by Coke Cola.)
6. Cleaning plaque and deposits from the teeth of human beings by drinking "energized" water;
7. Coal strip mining (particularly when large amounts of water are used);
8. Water based paints when spraying, and in their manufacture;
9. Lawn and garden liquid fertilizers or use to treat the irrigation water.

Viscosity

The viscosity of the aqueous and/or non-aqueous compositions may vary widely, depending upon the components and/or ingredients that are present therein, the levels of components and/or ingredients that are present therein, processing aids such as emulsifiers, and like considerations, but preferably ranges from about 0 to about 10,000 cp, and more preferably ranges from about 0 to about 1,000 cp. Viscosities of the compositions may be determined using a conventional viscometer. Table 1 below provides viscosities for several different substances.

TABLE 1

| Simple Liquids | T (° C.) | $\eta$ (mPa · s) |
| --- | --- | --- |
| alcohol, ethyl (grain) | 20 | 1.1 |
| alcohol, isopropyl | 20 | 2.4 |
| alcohol, methyl (wood) | 20 | 0.59 |
| Blood | 37 | 3-4 |
| ethylene glycol | 25 | 16.1 |
| ethylene glycol | 100 | 1.98 |
| Mercury | 15 | 1.55 |
| Milk | 25 | 3 |
| oil, vegetable, canola | 25 | 57 |
| oil, vegetable, canola | 40 | 33 |
| oil, vegetable, corn | 20 | 65 |
| oil, vegetable, corn | 40 | 31 |
| oil, vegetable, olive | 20 | 84 |
| oil, vegetable, olive | 40 | ?? |
| oil, vegetable, soybean | 20 | 69 |
| oil, vegetable, soybean | 40 | 26 |
| oil, machine, light | 20 | 102 |
| oil, machine, heavy | 20 | 233 |
| oil, motor, SAE 10 | 20 | 65 |
| oil, motor, SAE 20 | 20 | 125 |
| oil, motor, SAE 30 | 20 | 200 |
| oil, motor, SAE 40 | 20 | 319 |
| propylene glycol | 25 | 40.4 |
| propylene glycol | 100 | 2.75 |
| Water | 0 | 1.79 |
| Water | 20 | 1.00 |
| Water | 40 | 0.65 |
| Water | 100 | 0.28 |

| Gases | T (° C.) | $\eta$ (µPa · s) |
| --- | --- | --- |
| Air | 15 | 17.9 |
| Hydrogen | 0 | 8.42 |
| Helium | 0 | 18.6 |
| Nitrogen | 0 | 16.7 |
| Oxygen | 0 | 18.1 |

| complex materials | T (° C.) | $\eta$ (Pa · s) |
| --- | --- | --- |
| Caulk | 20 | 1000 |
| glass, room temperature | | $10^{18}$-$10^{21}$ |
| glass, strain point | | $10^{13.6}$ |
| glass, annealing point | | $10^{12.4}$ |
| glass, softening | | $10^{6.6}$ |
| glass, working | | $10^{3}$ |
| glass, melting | | $10^{2}$ |
| Honey | 20 | 10 |
| Ketchup | 20 | 50 |
| Lard | 20 | 1000 |
| Molasses | 20 | 5 |

TABLE 1-continued

| Mustard | 25 | 70 |
| --- | --- | --- |
| peanut butter | 20 | 150-250 |
| sour cream | 25 | 100 |
| syrup, chocolate | 20 | 10-25 |
| syrup, corn | 25 | 2-3 |
| syrup, maple | 20 | 2-3 |
| Tar | 20 | 30,000 |
| vegetable shortening | 20 | 1200 |

1 centipoise (cP) = 1 millipascal second ($\eta$ (mPa · s))

PH

The pH of the aqueous and/or non-aqueous compositions may also vary widely, and preferably ranges from about 2 to about 13, and more preferably ranges from about 6 to about 10, and may be adjusted downward or upward using substances and methods known by those of skill in the art, such as acids (citric acid and the like) to decrease the pH or bases (sodium hydroxide and the like) to increase the pH.

Preparation of Compositions

The aqueous and/or non-aqueous compositions, and diluted forms thereof, can be prepared by "energizing" the compositions, one or more components therein and/or water (or another aqueous composition) that is used for dilution purposes in the manner described hereinabove. Other steps, methods and equipment that may be used to prepare the compositions, or to dilute aqueous or non-aqueous compositions, are conventional, and are known by those of skill in the art. For example, agitation of an aqueous composition that has been diluted with water may be achieved using a standard mixer, at a slow, moderate or even vigorous speed.

Packaging

The compositions of the invention may be packaged in any suitable manner for packaging liquid products, such as a plastic, metal or glass jar, bottle or other container.

Use of the Compositions

The aqueous and non-aqueous compositions of the invention, and/or water (or another aqueous composition) employed to dilute such compositions, may be used at a temperature generally ranging from about 40° F. to about 220° F. while at a pressure ranging from about 0 to about 60 psi, and preferably ranging from about 60° F. to about 212° F. while at a pressure ranging from about 1 to about 120 psi, with ambient temperature and a pressure of about 60 psi being most preferred. Those of ordinary skill in the art may readily determine an optimal pressure to use in connection with a particular temperature. For example, for cleaning purposes, room temperature or higher is preferred, and greater results may be achieved at higher temperatures, such as up to about 220° F. if under pressure of about 45-60 psi., which present steam flashing that allows particularly effective cleaning. However, once an aqueous solution, one or more components therein and/or a diluting agent, such as water, flashes to steam as a result of a high temperature and/or pressure, and subsequently re-condenses to water vapor, the water vapor would generally need to be re-energized one or a plurality of times in order for it to produce the most effective results (generally one time). Although such re-energizing is preferred, it is not critical. For example, in a steam generation plant, such water vapor is generally recycled to a water makeup tank, and becomes part of boiler feed water that is employed to generate steam. Another example of the use of such high temperatures and/or pressures would be with a steam-cleaning machine, such as a carpet steam cleaner or a dry cleaner.

The quantity of a composition of the invention to be used for each application depends upon the nature of the composition, the particular use being made and the area of an object involved, and may vary widely, but may readily be determined by those of skill in the art using the information contained herein. However, the amount of the composition that is employed per each application preferably ranges from about 1 mL to about 10 L, and more preferably ranges from about 10 mL to about 5 L, and still more preferably ranges from about 100 mL to about 2 L, and even still more preferably ranges from about 500 mL to about 1 L, with about 750 mL being most preferred. For example, about 750 mL of the composition may be applied to a surface of an object from a suitable container or applicator and spread over, or rubbed onto or into, the object using the hands or fingers, or a suitable application or other device.

The number of applications of a composition of the invention to an object that will generally be effective for producing a particular result, may vary widely, depending upon a variety of factors, such as the concentration of the composition, the amount of the composition that is applied to an object, the condition of the object, and like factors, and may readily be determined by those of skill in the art. Preferably, one or more applications (one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty and so forth applications) are made to an object over a period of at least about one minute, hour, day or week, or a series of minutes, hours, days or weeks (one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine and so forth minutes, hours, days or weeks) will be effective for producing the desired result.

Generally, the higher the number of applications of the composition of the invention to an object within a period of time, the greater an improvement will be observed or otherwise detected in connection with the object, and the less time will be required for achieving such results. Although there generally is no limit to the number of applications of the composition that can be applied to the object, above a certain number of applications, no further improvement may be observed or otherwise detected.

It is most preferable that at least about 4 applications of the composition are applied to an object over a period of about 2 minutes. It is more preferable that at least about 2 applications of the composition are applied to an object over a period of about 2 minutes. It is still more preferable that at least about 2 applications of the composition are applied to the object over a period of about 1 minute.

The compositions of the invention can be applied to an object or surface in any conventional manner using conventional equipment, for example, via spraying, such as with a spray pump or an aerosol spray can, brushing, pouring, wiping, coating, spray showers, garden hose and/or mopping. In the experiments that are described in the "Examples" section, tape was employed to attach an opposing set of two magnets having a Gauss strength of 3500 Gauss each to the lower sides of: (a) a plastic spray bottle; and (b) a tin can of APC.

Effects of "Energized" Compositions

While not wishing to be bound by any particular theory, aqueous and/or non-aqueous compositions appear to become "vitalized" (i.e. to receive energy) when there are "energized," and to transfer some or all of this energy to one or more other components that are present in the compositions (if any), and/or to one or more substances that a user of the "energized" compositions is attempting to remove from a surface or area that is being cleaned, such as dirty motor oil that has leaked from a vehicle onto an asphalt driveway. This appears to have an effect of enabling the composition to move more rapidly, and/or to displace the substances(s) more rapidly, more readily, and in a safer manner in comparison with the same composition that has not been "energized."

The amount of energy that is transferred to the composition when it is "energized" is difficult to prove scientifically, but the results of experiments that are described herein, and the corresponding figures (photographs), clearly show very significant advantages of using a composition that has been "energized" to clean in comparison with the same composition that has not been "energized".

Teeth Cleaning and Whitening

The present invention also provides a method for removing calcium deposits, plaque deposits and/or stains from, and/or whitening, one or more teeth of a human or animal subject comprising having the subject drink an amount of water (or other aqueous composition) that has been "energized" with one or more magnets for a period of time that is effective for removing calcium deposits, plaque deposits or stains from, or whitening, the teeth of the subject, wherein the water is "energized" by positioning the one or more magnets in a manner that one or more magnetic forces or magnetic fields are created on or over the water, wherein the one or more magnets have a combined Gauss strength ranging from about 100 to about 10,000, and wherein the water is "energized" just prior to use, preferably during use, and most preferably at the point of use.

While a wide variety of aqueous compositions may be used in this method, it is preferred that steam distilled water and/or mineral water be used. The aqueous compositions may be "energized" in the manner described herein.

Generally, the amount of water (or other aqueous composition) that is effective for removing calcium deposits, plaque deposits and/or stains from, and/or whitening, the teeth of a subject ranges from about 1,000 to about 8,000 mL per day, and preferably ranges from about 3,500 to about 8,000 mL per day, and still more preferably ranges from about 6,000 to about 8,000 mL per day.

Generally, the period of time that is effective for removing calcium deposits, plaque deposits and/or stains from, and/or whitening, the teeth of the subject is at least about 180 days, and is preferably at least about 360 days, and is more preferably at least about 360 days. Beyond these periods of time, no additional cleaning and/or whitening effects may be seen.

It is recommended that such teeth whitening and/or cleaning be performed under the guidance of a dentist and/or physician. Long term effects of this method on the human body have not yet been studied.

Sources of Ingredients

All of the ingredients, materials and equipment employed in the examples, and generally employed in the methods of the invention, and to produce the compositions of the invention, are commercially available from sources known by those of skill in the art, such as PepsiCo, Inc. (Purchase, N.Y.), Coca-Cola Company (Atlanta, Ga.), Deer Park Water Co. (Wilkes Barre, Pa.), Fiji Water (Los Angeles, Calif.), Virgin Waters Limited (Eatonville, Wash.), Dekalb County Department of Water Management, (Atlanta, Ga.), Sky King Distilled Water (Ashville, N.C.), DS Waters of America, (Atlanta, Ga.), Hydro Systems, (Cincinnati, Ohio), Eneflux Armtek Magnetics, (Bethpage, N.Y.), Orbit Irrigation Products, (Bountiful, Utah), Inmark North America, (Austell, Ga.), Dura Magnets, Inc. (Sylvanie, Ohio), K & J Magnetics, Inc. (Jamison, Pa.), ALL Magnetics, Inc. (Anaheim, Calif.), The Electrodyne Company, Inc. (Batavia, Ohio), The Telechem Corporation (Atlanta, Ga.), Sunshine Makers, Inc. (Huntington Harbour, Calif.), The Clorox Company, (Oakland, Calif.)

The following examples describe and illustrate the compositions and methods of the present invention. These examples are intended to be merely illustrative of the present invention, and not limiting thereof in either scope of spirit. Those of skill in the art will readily understand that variations of certain of the conditions and/or steps employed in the procedures described in the examples can be employed.

EXAMPLE 1

Preparation of "Energized" Dasani Water

In this experiment two types of "energized" Dasani water were prepared and compared with a control (non-energized Dasani water). Three bottles (16.9 ounces each) of Dasani water were procured from a grocery store. Bottle #1 was not "energized", and bottles #2 and #3 were "energized" in the manner described below, and at different energy levels. This experiment was conducted at ambient temperature.

Bottle No. 2

A conventional bottle sleeve that fit snugly around the bottle, that was approximately the length of the bottle, and that enclosed the bottom of the bottle (the part that can rest upon a surface), but not the top, was placed around bottle #2. The bottom of the cloth sleeve contained six disc shaped magnets that were each approximately 3/16 inches thick, and 3/8 inch in diameter, and that were in full contact with the bottom of the bottle. (The bottom of the bottle could conveniently rest on the magnets, each of which was horizontally positioned in a manner that it could lay flat upon a surface. The magnets were spaced apart from each other by the same distance, which was about ½ to ¾ of an inch.) The strength of each magnet was approximately 150 Gauss, providing a total Gauss strength (of all of the magnets combined) of about 900 Gauss. The magnet-containing sleeve was left on the bottle for a period of several 1 minute.

Bottle No. 3

The water in bottle #3 was "energized" to a significantly greater extent in comparison with the water in bottle #2, which was accomplished using more powerful magnets for bottle #3 (magnets that were 7 to 8 times more powerful in comparison with the magnets used for bottle #2). Although it is not possible to determine the level of energy that the water in bottle #2 or bottle #3 included, it is clear that magnets that were 7 to 8 times more powerful would create a larger magnetic field, and would effect a larger quantity of the liquid at one time, probably producing a more "energized" solution percentage wise.

A sleeve (shown in FIG. 39) made from cloth that fit snugly around the bottle, and that was approximately the length of the bottle, but that did not enclose the top or bottom of the bottle, was placed around bottle #3. Instead of disc magnets, bottle #3 had two rectangular magnets placed on opposite sides of the bottle, each of which was about 1.5×2×0.75 inches and about 3500 Gauss. The magnet-containing sleeve was left on the bottle for a period of 1 minute.

The water that was present in bottle #1, bottle #2 and bottle #3 at the conclusion of this experiment was tasted. The water in bottle #1 tasted like regular Dasani water. In contrast, the water in bottle #2 had a metal taste, and the water in bottle #3 had a metal taste that was significantly stronger than the metal taste of the water that was contained in bottle #2.

EXAMPLE 2

Preparation of Diluted Cleaning Solution with "Energized" Water

Simple Green® All-Purpose Cleaner is diluted in the manner described below using only "energized" tap water. The dilutions are made immediately after the tap water is "energized," and the tap water is "energized" using two magnets, each having a strength of 3500 Gauss, fastened to opposite sides of a bottle containing the tap water.

Heavy Cleaning

1:1 up to 1:10 Dilution (Example: 1 oz. Simple Green® to 1 cup water)

Light Cleaning

1:30 Dilution (Example: 1 oz. Simple Green® to 4 cups water)

Stains

1:1 Dilution (Example: 1 oz. Simple Green® to 1 oz. water)

EXAMPLE 3

Removal of Motor Oil From Non-Stick Cake Pans Using "Energized" or Non-"Energized" Water as a Cleaning and/or Rinsing Agent In this experiment, a series of four separate tests were performed involving a removal of motor oil from non-stick cake pans using an aqueous liquid (100% tap water or 100% steam distilled water) that had not been "energized" in comparison with the same aqueous liquid that had first been "energized." Each test used two 4.5" non-stick cake pans ("pans"), and had a duration of 14 minutes. All tests were conducted at ambient temperature, and all products being "energized" were at room temperature. With the exception of APC, all "energized" products that were used in this experiment were "energized" by placing them (separately) in a conventional trigger spray plastic bottle having two magnets, each having a strength of 3500 Gauss, fastened to opposite sides of the bottle. APC (present in a metal can) was also "energized" using two magnets, each having a Gauss strength of 3500, attached to opposite sides of its can. The products typically remained in the bottles or cans (being "energized" by the magnets) for an amount of time that was required to set up the particular test, which was generally a period of about 1 to 2 minutes.

Unless described differently in connection with a particular test, for each of the four tests, 3 ml (about one teaspoon) of dirty motor oil (obtained from a vehicle oil change shop) was poured separately onto the bottom (upper surface) of each of the two pans, as is shown in FIG. 1. The first pan (pan #1) was then sprayed 7 separate times with an aqueous liquid (100% tap water or 100% steamed distilled water purchased from Sky King Distilled Water (Ashville, N.C.) or APC that had not been "energized." With each spray, approximately 10-11 ml of the aqueous liquid was sprayed onto the pan, using a conventional plastic spray bottle with a trigger sprayer (shown in FIG. 2). The second pan (pan #2) was sprayed 7 times in the same manner as pan #1, and with the same amount of the aqueous liquid, using the same aqueous liquids, with the exception that the aqueous liquids had been "energized" using magnets for several minutes prior to their use in pan #2 ("energized" 100% tap water, 100% distilled water or APC).

After each pan was sprayed 7 times with the aqueous liquid, each pan was allowed to sit for 7 minutes with the oil and non-energized or "energized" liquid present thereon (to rest right side up upon a surface). At the conclusion of this 7-minute period, each pan was turned upside down on a surface to allow the oil and aqueous liquid to drain off of the pan onto the surface for 7 minutes. At the conclusion of the second 7-minute period, the pans were each returned right side up and rested on a surface. Then, the oil dispersion in each of the pans, and the difference in the oil dispersion between the two pans, was observed. As is described below, and as is shown in the figures, the difference in the oil dispersion between the two pans was very significant. In each of the figures that resulted from these tests, and that contain two pictures in the same figure, the pan to which a non-energized aqueous liquid was sprayed is shown on the left side, and the pan to which an "energized" aqueous liquid was sprayed is shown on the right side.

Test No. 1—Tap Water

In this test, the aqueous liquid that was sprayed into the pans was 100% tap water (in a non-energized form for pan #1, and in an "energized" form for pan #2).

Photographs that were taken in connection with this test are shown in FIGS. 1, 2, 3, 4, 5 and 6.

FIG. 1 is a photograph showing pan #1 (left side) and pan #2 (right side) after 3 mL of dirty motor oil was poured onto the upper surface of the bottom of each pan, and prior to spaying either pan with an aqueous liquid.

Figure 2:
FIG. 2 is a photograph showing a spray bottle that was used in Example 3 to spray an aqueous liquid that had not been "energized" onto pan #1 in Test No. 1 of Example 3.

FIG. 2 is a photograph showing a spray bottle that was used to spray the aqueous liquid that had not been "energized" onto pan #1.

Figure 3:
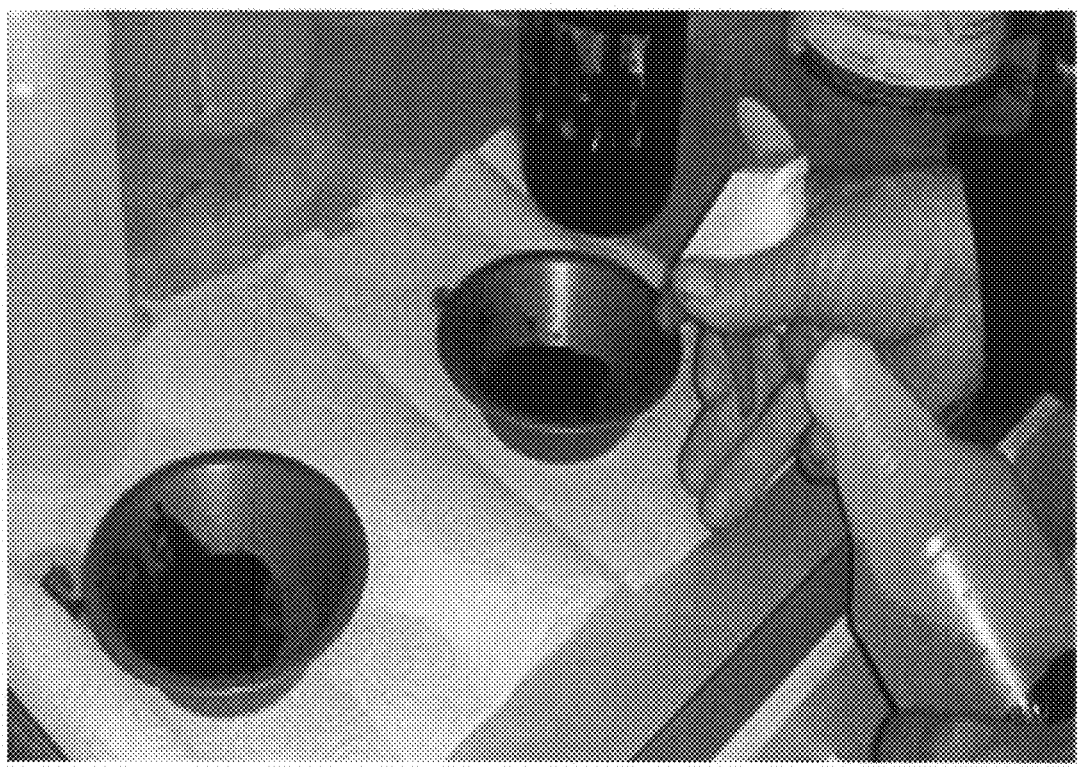
FIG. 3 is a photograph showing a spray bottle that is spraying 100% tap water that had been "energized" onto pan #2 in Test No. 1 of Example 3.

FIG. 3 is a photograph showing the spray bottle that is spraying 100% tap water that has been "energized" onto pan #2.

Figure 4:
FIG. 4 is a photograph showing in Test No. 1 of Example 3: (a) non-stick cake pan #1 (left side) just after it had been sprayed with 7 applications of 100% tap water that had not been "energized"; and (b) non-stick cake pan #2 (right side) just after it had been sprayed with 7 applications of 100% tap water that had been "energized."

FIG. 4 is a photograph showing: (a) pan #1 (left side) just after it had been sprayed with 7 applications of 100% tap water that had not been "energized"; and (b) pan #2 (right side) just after it had been sprayed with 7 applications of 100% tap water that had been "energized." Each pan appears in this photograph to include a visually equivalent volume of a water and oil.

Figure 5:
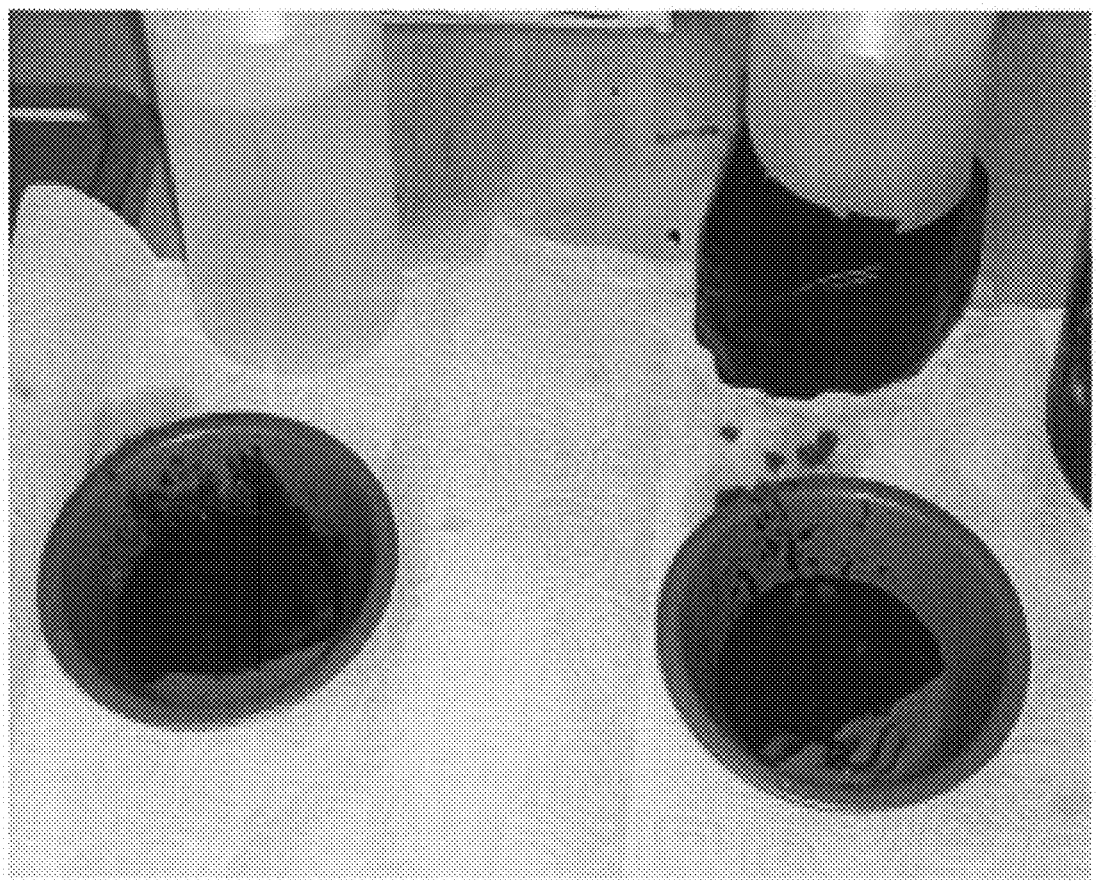
FIG. 5 is a photograph showing in Test No. 1 of Example 3: (a) non-stick cake pan #1 (left side) after having sat for 7 minutes (after it had been sprayed with 7 applications of 100% tap water that had not been "energized"); and (b) non-stick cake pan #2 (right side) after having sat for 7 minutes (after it had been sprayed with 7 applications of 100% tap water that had been "energized").

FIG. 5 is a photograph showing: (a) non-stick cake pan #1 (left side) after having sat for 7 minutes (after it had been sprayed with 7 applications of 100% tap water that had not been "energized"); and (b) non-stick cake pan #2 (right side) after having sat for 7 minutes (after it had been sprayed with 7 applications of 100% tap water that had been "energized"). This photograph shows that the adhesion of the oil to pan #2 has undergone a change, and that the oil has begun to lift and "wipe" away (disassociate itself) from the pan. In contrast, this photograph also shows that the oil in pan #1 does not appear to have undergone such a change, or to be lifting or disassociating itself from the pan.

Figure 6:
FIG. 6 is a photograph showing in Test No. 1 of Example 3: (a) non-stick cake pan #1 (left side) after having been turned upside down on a counter to allow the dirty motor oil and aqueous liquid to drain off of the pan onto the surface for 7 minutes (after it had been sprayed with 7 applications of 100% tap water that had not been "energized" and allowed to sit for 7 minutes); and (b) non-stick cake pan #2 (right side) after having been turned upside down on a counter to allow the dirty motor oil and aqueous liquid to drain off of the pan onto the surface for 7 minutes (after it had been sprayed with 7 applications of 100% tap water that had been "energized" and allowed to sit for 7 minutes).

FIG. 6 is a photograph showing: (a) non-stick cake pan #1 (left side) after having been turned upside down on a counter to allow the oil and aqueous liquid to drain off from the pan onto the counter for 7 minutes; and (b) non-stick cake pan #2 (right side) after having been turned upside down on a counter to allow the oil and aqueous liquid to drain off from the pan onto the counter for 7 minutes. A dramatic difference can be seen in FIG. 6 between these two pans. Although the amounts of water and oil that had been applied to each pan had been equal, the oil showed a significantly greater reaction to the "energized" water in pan #2 in comparison with the non-energized water in pan #1. In pan #2, the oil appears to have dispersed and disassociated itself from the pan to a significantly greater extent in comparison with pan #1, thereby permitting the oil to be removed from the pan simply by sliding and/or falling off of the pan as a result of gravitational forces. In contrast with pan #2, the oil in pan #1 appears to be strongly adhering to the pan. Pan #2 appears to have only a very small percentage of oil remaining in the pan (i.e., it is almost clean and free of the oil because the oil has almost been completely released from the pan), whereas pan #1 appears to have a large percentage of the oil remaining in the pan (i.e., it appears to be very dirty and full of oil that is adhering to the surfaces of the pan).

This test shows that 100% tap water that has been "energized" appears to have an ability to cause dirty motor oil to disperse from a non-stick cake pan and clean the pan, whereas 100% tap water that has not been "energized" does not have this ability (under the same set of circumstances). Such "energized" tap water (i.e. not including any other chemical agents or substances), thus, can be employed to clean a variety of different objects and/or surfaces, such as a vehicle, or the driveway and/or entrance to a store in a typical "Gas and Go" operation, advantageously avoiding the use of harsh chemicals, and the significant costs associated therewith.

Test No. 2—Steamed Distilled Water

In this test, the aqueous liquid that was sprayed into the pans was 100% steamed distilled water (in a non-energized form for pan #1, and in an "energized" form for pan #2).

Photographs that were taken in connection with this test are shown in FIGS. 7, 8, 9, 10 and 11.

Figure 7:
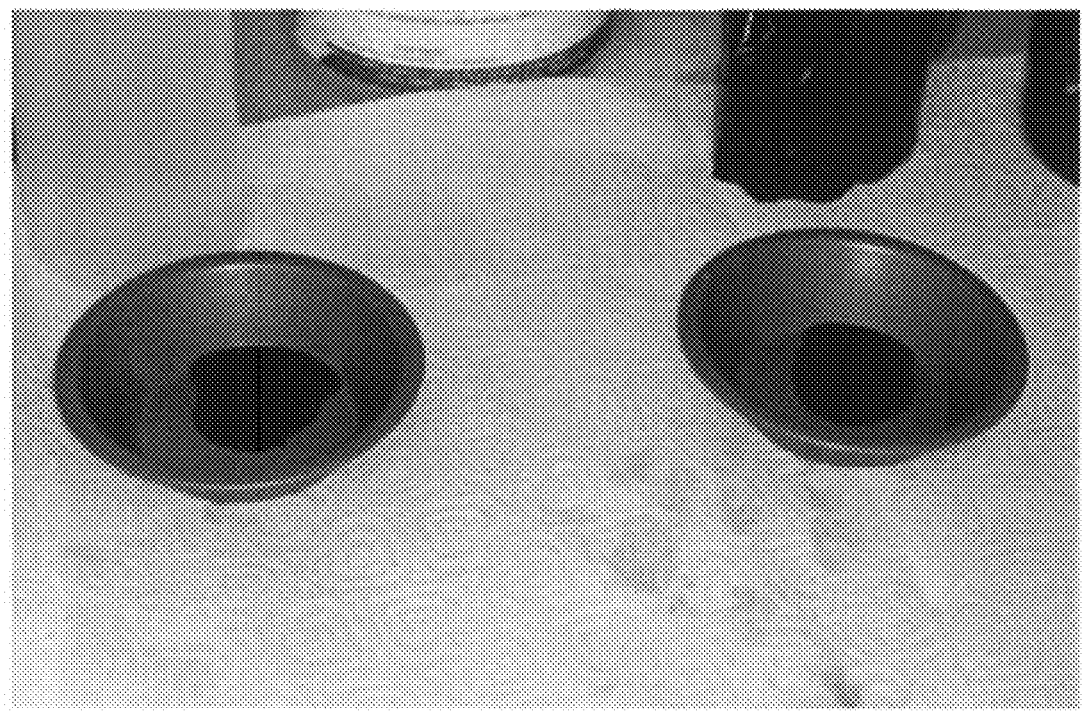
FIG. 7 is a photograph showing a perspective view of non-stick cake pan #1 (left side) and non-stick cake pan #2 (right side) after 3 mL of dirty motor oil was poured onto the upper surface of the bottom of each pan in Test No. 2 of Example 3, and prior to spaying either pan with an aqueous liquid.

FIG. 7 is a photograph showing pan #1 (left side) and pan #2 (right side) after 3 mL of dirty motor oil was poured onto the upper surface of the bottom of each pan, and prior to spaying either pan with an aqueous liquid.

Figure 8:
FIG. 8 is a photograph showing in Test No. 2 of Example 3: (a) non-stick cake pan #1 (left side) just after it had been sprayed with 7 applications of 100% steam distilled water that had not been "energized"; and (b) non-stick cake pan #2 (right side) just after it had been sprayed with 7 applications of 100% steam distilled water that had been "energized."

FIG. 8 is a photograph showing: (a) pan #1 (left side) just after it had been sprayed with 7 applications of 100% steamed distilled water that had not been "energized"; and (b) pan #2 (right side) just after it had been sprayed with 7 applications of 100% steam distilled water that had been "energized." Each pan appears in this photograph to include a visually equivalent volume of a water and oil.

Figure 9:
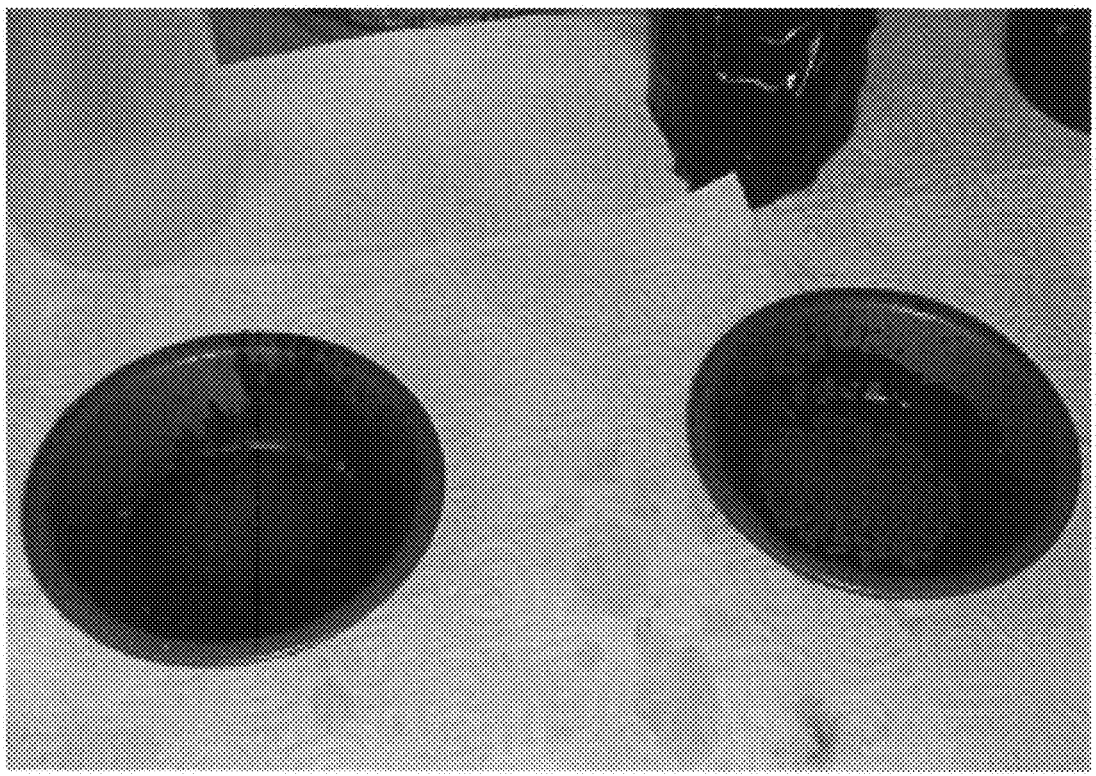
FIG. 9 is a photograph showing in Test No. 2 of Example 3: (a) non-stick cake pan #1 (left side) after having sat for 7 minutes (after it had been sprayed with 7 applications of 100% steam distilled water that had not been "energized"); and (b) non-stick cake pan #2 (right side) after having sat for 7 minutes (after it had been sprayed with 7 applications of 100% steam distilled water that had been "energized").

FIG. 9 is a photograph showing: (a) non-stick cake pan #1 (left side) after having sat for 7 minutes (after it had been sprayed with 7 applications of 100% steam distilled water that had not been "energized"); and (b) non-stick cake pan #2 (right side) after having sat for 7 minutes (after it had been sprayed with 7 applications of 100% steam distilled water that had been "energized"). This photograph shows that the adhesion of the oil to pan #2 has undergone a change, and that the oil has begun to lift and "wipe" away (disassociate itself) from the pan. In contrast, this photograph also shows that the oil in pan #1 does not appear to have undergone such a change, or to be lifting or disassociating itself from the pan.

Figure 10:
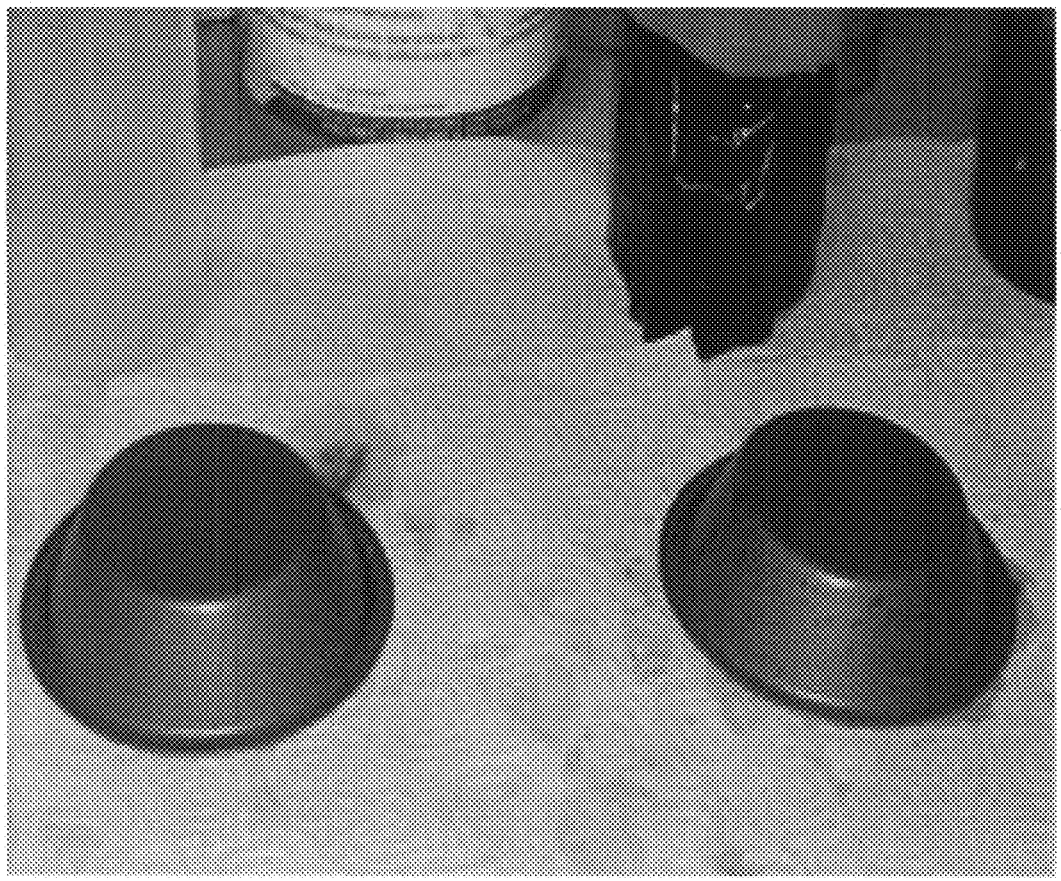
FIG. 10 is a photograph showing in Test No. 2 of Example 3: (a) non-stick cake pan #1 (left side) after having been turned upside down onto a counter to allow the dirty motor oil and aqueous liquid to drain off of the pan onto the surface; and (b) non-stick cake pan #2 (right side) after having been turned upside down onto a counter to allow the motor oil and aqueous liquid to drain off of the pan onto the surface.

FIG. 10 is a photograph showing: (a) non-stick cake pan #1 (left side) after having been turned upside down onto a counter to allow the oil and aqueous liquid to drain off of the pan onto the surface; and (b) non-stick cake pan #2 (right side) after having been turned upside down onto a counter to allow the oil and aqueous liquid to drain off of the pan onto the surface.

Figure 11:
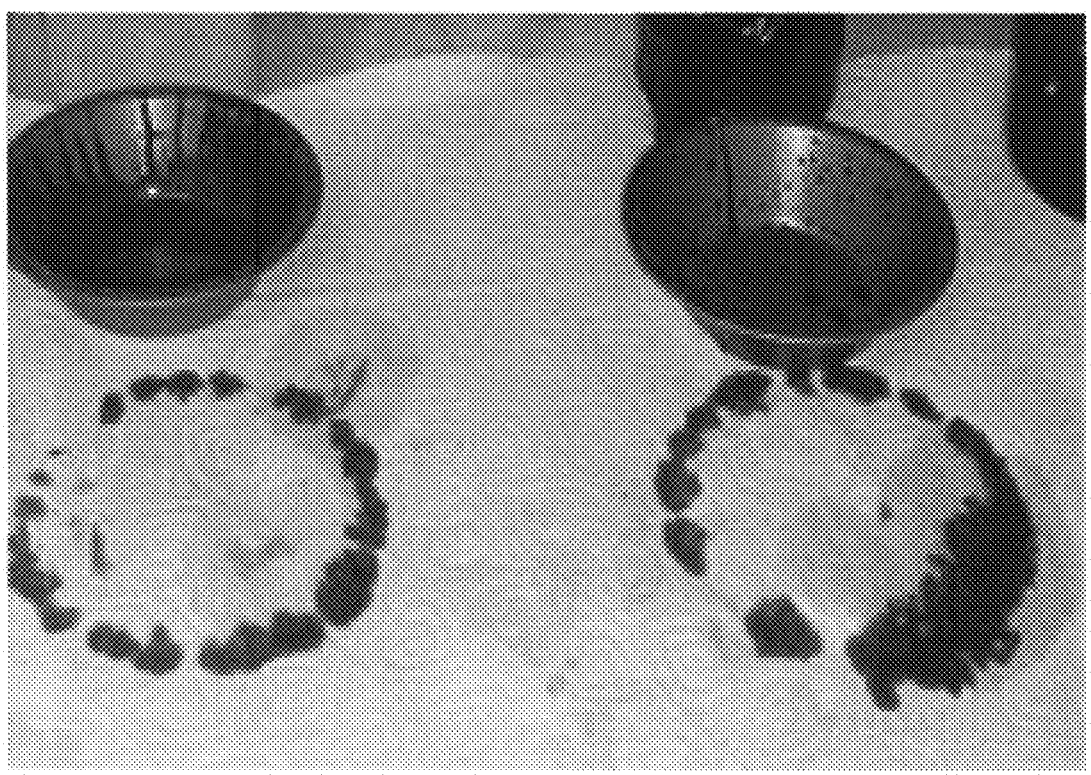
FIG. 11 is a photograph showing in Test No. 2 of Example 3: (a) non-stick cake pan #1 (left side) after having been turned upside down on a counter to allow the dirty motor oil and aqueous liquid to drain off of the pan onto the surface for 7 minutes (after it had been sprayed with 7 applications of 100% steam distilled water that had not been "energized" and allowed to sit for 7 minutes); and (b) non-stick cake pan #2 (right side) after having been turned upside down on a counter to allow the dirty motor oil and aqueous liquid to drain off of the pan onto the surface for 7 minutes (after it had been sprayed with 7 applications of 100% steam distilled water that had been "energized" and allowed to sit for 7 minutes).

FIG. 11 is a photograph showing: (a) non-stick cake pan #1 (left side) after having been turned upside down on a counter to allow the oil and aqueous liquid to drain off from the pan onto the counter for 7 minutes; and (b) non-stick cake pan #2 (right side) after having been turned upside down on a counter to allow the oil and aqueous liquid to drain off from the pan onto the counter for 7 minutes. A dramatic difference can be seen in FIG. 11 between these two pans. Although the amounts of water and oil that had been applied to each pan had been equal, the dirty motor oil showed a significantly greater reaction to the "energized" water in pan #2 in comparison with the non-energized water in pan #1. In pan #2, the oil appears to have dispersed and disassociated itself from the pan to a significantly greater extent in comparison with pan #1, thereby permitting the oil to be removed from the pan simply by sliding and/or falling off of the pan as a result of gravitational forces. In contrast with pan #2, the oil in pan #1 appears to be strongly adhering to the pan. Pan #2 appears to have only a very small percentage of oil remaining in the pan (i.e., it is almost clean and free of the oil because the oil has almost been completely released from the pan), whereas pan #1 appears to have a large percentage of the oil remaining in the pan (i.e., it appears to be very dirty and full of oil that is adhering to the surfaces of the pan).

This test shows that 100% steamed distilled water (i.e. the purist aqueous liquid of all) that has been "energized" appears to have an ability to cause oil to disperse from a non-stick cake pan and clean the pan, whereas 100% steam distilled water that has not been "energized" does not have this ability (under the same set of circumstances).

Test No. 3—Tap Water vs. "Energized" All Purpose Cleaner

Figure 12:
FIG. 12 is a photograph showing in Test No. 3 of Example 3: (a) non-stick cake pan #1 (left side) to which 3 mL of dirty motor oil had been added just after the pan (and motor oil) had been sprayed with 10 mL of 100% tap water that had not been "energized"; and (b) non-stick cake pan #2 (right side) to which 3 mL of dirty motor oil had been added just after the pan (and motor oil) had been sprayed with 10 mL of "energized" All Purpose Cleaner ("APC").
Figure 13:
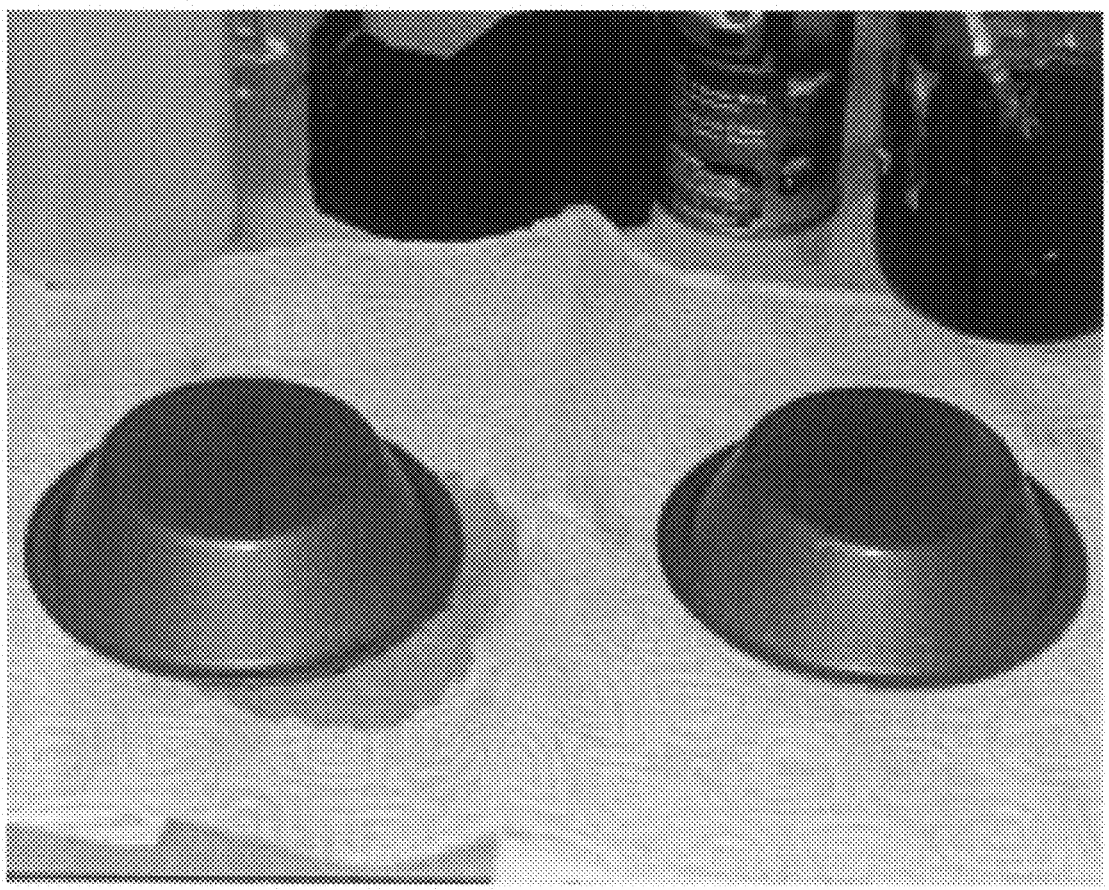
FIG. 13 is a photograph showing in Test No. 3 of Example 3 both pan #1 (left side) and pan #2 (right side) after the pans had been turned upside down on a counter for less than ten seconds.
Figure 14:
FIG. 14 is a photograph showing in Test No. 3 of Example 3 both pan #1 (left side) and pan #2 (right side) after the pans had been placed upon their side and allowed to drain for about 7 minutes.
Figure 15:
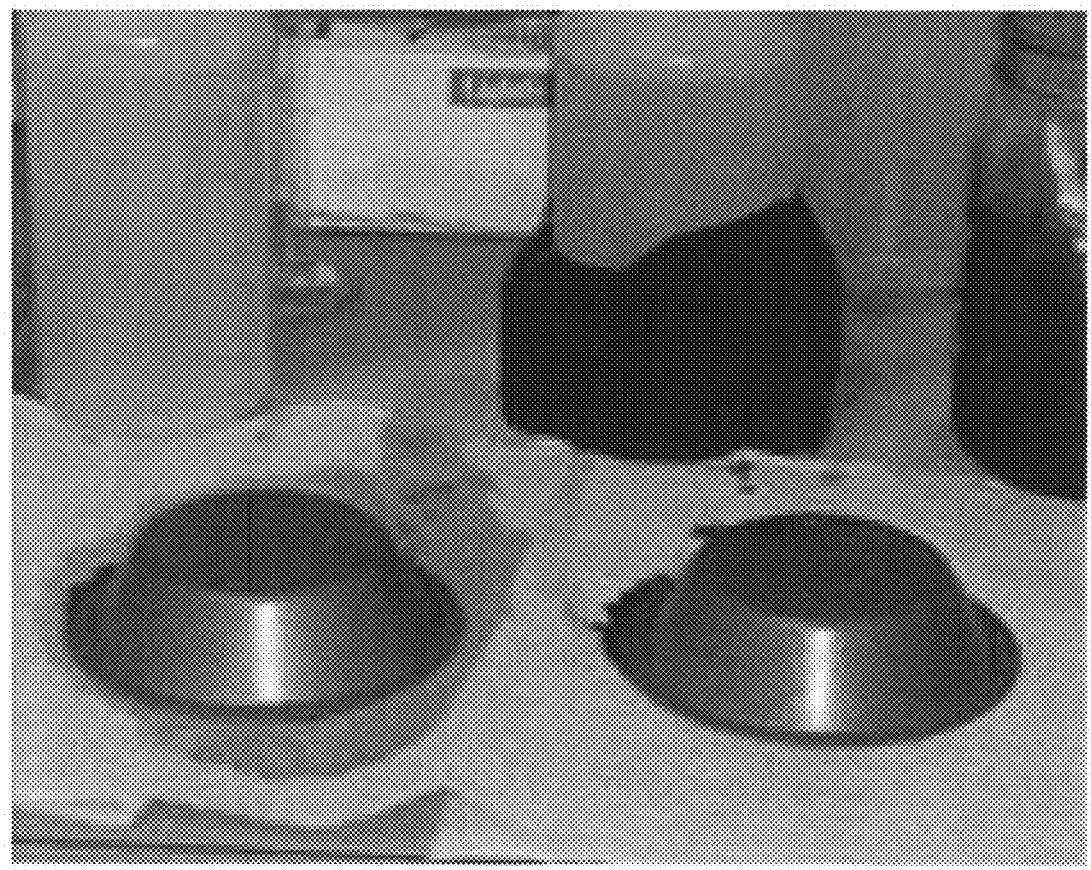
FIG. 15 is a photograph showing in Test No. 3 of Example 3 pan #1 (left side) after it had been sprayed one time with 10 mL of 100% tap water that had not been "energized," and pan #2 (right side) after it had been sprayed one time with 10 mL of 100% tap water that had been "energized," and immediately placed upside down on the surface of a counter for about 7 minutes.
Figure 16:
FIG. 16 is a photograph showing in Test No. 3 of Example 3 both pan #1 (left side) and pan #2 (right side) after the pans had been placed on their sides for a period of 7 minutes.
Figure 17:
FIG. 17 is a photograph showing in Test No. 3 of Example 3 both pan #1 (left side) and pan #2 (right side) after the pans had been permitted to rest on their sides for an additional 7 minutes.

Test No. 3 varied somewhat from Test No. 1 and Test No. 2. In Test No. 3, after 3 mL each of dirty motor oil was placed onto the surfaces of pan #1 and pan #2, 10 mL of 100% tap water that had not been "energized" was sprayed onto pan #1, and 10 mL of All Purpose Cleaner ("APC") that had been "energized" was sprayed onto pan #2 as a cleaning agent (FIG. 12). APC has a water content of about 66%. Both pans were then turned upside down on a counter for less than ten seconds (FIG. 13), and subsequently placed onto their side and allowed to drain for about seven minutes (FIG. 14). Thereafter, pan #1 was sprayed with 10 mL of 100% tap water that had not been "energized", and pan #2 was sprayed with 10 mL of 100% tap water that had been "energized" (both sprays being used as rinsing agents). Both pans were then immediately placed upside down on the counter for a period of about seven minutes (FIG. 15), and thereafter placed on their sides for a period of about seven minutes (FIG. 16). Both pans were then sprayed a second time (in the same manner as the first time) and permitted to rest for an additional seven minutes (FIG. 17). Then, pan #1 was sprayed 7 additional times with 100% tap water that had not been "energized" (10-11 mL per spray), and pan #2 was sprayed 7 additional times with 100% tap water that had been "energized," with all sprays being used as rinsing agents. The same "energized" water than had been employed previously in this test was employed again at this stage of the test. Both pans were then permitted to rest on their sides for a period of about seven minutes.

Figure 18:
FIG. 18 is a photograph showing in Test No. 3 of Example 3 both pan #1 (left side) and pan #2 (right side) at the conclusion of Test No. 3.

FIG. 18 shows pan #1 (left side) and pan #2 (right side) at the conclusion of this test, and a dramatic difference can be seen between pan #1 and pan #2. Although the amounts of oil that had been applied to each pan had been equal, the oil showed a significantly greater reaction to the "energized" water (rinsing agent) in pan #2 in comparison with the non-energized water (rinsing agent) in pan #1. In pan #2, the oil appears to have dispersed and disassociated itself from the pan to a significantly greater extent in comparison with pan #1, thereby permitting the oil to be removed from the pan simply by sliding and/or falling off of the pan as a result of gravitational forces. In contrast with pan #2, the oil in pan #1 appears to be strongly adhering to the pan. Pan #2 appears to have only a very small percentage of oil remaining in the pan (i.e., it is almost clean and free of the oil because the oil has almost been completely released from the pan), whereas pan #1 appears to have a large percentage of the oil remaining in the pan (i.e., it appears to be very dirty and full of oil that is adhering to the surfaces of the pan).

In comparison with Test No. 1 and Test No. 2, in which no cleaning agent was separately employed, APC was used in Test No. 3 on pan #2 as a cleaning agent. The results of Test No. 3 showed a higher percentage of cleaning and rinsing of the oil from pan #2, and in a shorter period of time, in comparison with the results of Test No. 1 and Test No. 2.

Test No. 3 also shows that a cleaning substance, such as APC, whether in an "energized" or non-energized form, can be used as a cleansing agent for objects and/or surfaces, with the cleansing agent being rinsed with 100% tap water that has been "energized" to clean spots or tougher stains in an enhanced manner in comparison with a rinse of 100% tap water (or another aqueous liquid) that has not been "energized".

Test No. 4—Non-Energized APC vs. "Energized" APC

Figure 19:
FIG. 19 is a photograph showing a perspective view of non-stick cake pan #1 (left side) and non-stick cake pan #2 (right side) after 3 mL of dirty motor oil was poured onto the upper surface of the bottom of each pan in Test No. 4 of Example 3, and prior to spaying either pan with an aqueous liquid.
Figure 20:
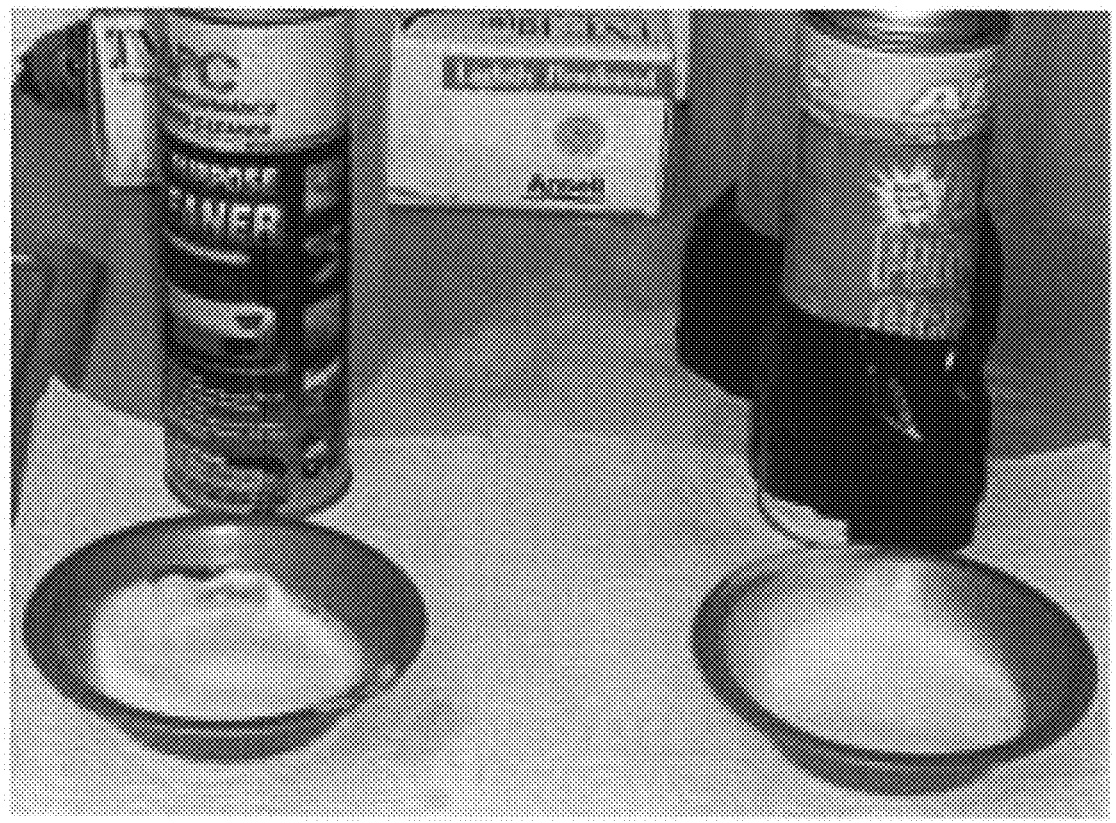
FIG. 20 is a photograph showing in Test No. 4 of Example 3: (a) non-stick cake pan #1 (left side) to which 3 mL of dirty motor oil had been added just after the pan (and motor oil) had been sprayed with 10 mL of non-energized APC; and (b) non-stick cake pan #2 (right side) to which 3 mL of dirty motor oil had been added just after the pan (and motor oil) had been sprayed with 10 mL of "energized" APC.
Figure 21:
FIG. 21 is a photograph showing in Test No. 4 of Example 3 non-stick cake pan #1 (left side) and non-stick cake pan #2 (right side) after having sat right side up on a counter for three minutes after the non-energized APC (pan #1) and "energized" APC (pan #2) were separately added to the pans.
Figure 22:
FIG. 22 is a photograph showing in Test No. 4 of Example 3 non-stick cake pan #1 (left side) and non-stick cake pan #2 (right side) after having been placed on their sides for a period of 7 minutes to permit the dirty motor oil and APC to drain therefrom.
Figure 23:
FIG. 23 is a photograph showing in Test No. 4 of Example 3 non-stick cake pan #1 (left side) and non-stick cake pan #2 (right side) less than 30 seconds after they were sprayed with either one application of 10 mL of 100% tap water that had not been "energized" (pan #1) or one application of 10 mL of 100% tap water that had been "energized" (pan #2).

Test No. 4 also varied somewhat from Test No. 1 and Test No. 2. In Test No. 4, after 3 mL each of dirty motor oil was placed onto the surfaces of pan #1 and pan #2 (FIG. 19), 10 mL of APC that had not been "energized" was sprayed onto pan #1, and 10 mL of APC that had been "energized" was sprayed onto pan #2, both being used as cleaning agents, and both foaming when present in the pans (FIG. 20). Then, the two pans were permitted to sit on a counter for three minutes (FIG. 21). Both pans were then placed on their sides for a period of three minutes to permit the oil and APC to drain therefrom (FIG. 22). FIG. 22 shows that a significantly higher percentage of oil drained off from pan #2 ("energized" APC) in comparison with pan #1 (non-energized APC). Thereafter, pan #1 was sprayed with one application of 10 mL of 100% tap water that had not been "energized", and pan #2 was sprayed with one application of 10 mL of 100% tap water that had been "energized" (both sprays being used as rinsing agents). FIG. 23 shows pan #1 and pan #2 immediately after they were sprayed. FIG. 23 shows a significantly greater draining of the oil from pan #2 ("energized" APC as cleaner and "energized" water as rinsing agent) in comparison with pan #1 (non-energized APC as cleaner and non-energized water as rinsing agent).

This test shows that "energizing" a cleaning liquid, such as APC, and a rinsing liquid, such as 100% tap water, result in a quicker cleaning time, an enhanced cleaning and an enhanced rinsing in comparison with a cleaning liquid and/or rinsing liquid that have not been "energized." The "energized" cleaning liquid (as well as the "energized" rinsing agent) likely exhibits these enhanced characteristics as a result of a transfer of energy to the oil.

EXAMPLE 4

Removal of Motor Oil From Non-Stick Cake Pans Using "Energized" or Non-Energized Rubbing Alcohol, Mouthwash, Coca Cola or Wine as a Cleaning Agent In this experiment, another series of four separate tests were performed involving a removal of oil from non-stick cake pans using one or four different aqueous liquids that had not been "energized" in comparison with the same aqueous liquid that had first been "energized." The aqueous liquids that were employed were: (1) rubbing alcohol (CVS Pharmacy, Atlanta, Ga.): (2) mouthwash—Blue Mint Antiseptic Mouth Rinse (CVS Pharmacy, Atlanta, Ga.); (3) Coca Cola (Coca Cola Company, Atlanta, Ga.); and (4) Zinfandel wine. Each test used two 4.5" non-stick cake pans ("pans"), and had a duration of from about seven to about ten minutes. All tests were conducted at ambient temperature, and all products were "energized" in the same manner as is described in Example 3.

Unless described differently in connection with a particular test, for each of the four tests 3 ml (about one teaspoon) of dirty motor oil was poured separately onto the upper surface of the bottom of each of the two pans. The first pan (pan #1) was then sprayed 7 separate times with one of the aqueous liquids (rubbing alcohol, mouthwash, wine or cola) that had not been "energized". With each spray, approximately 10-11 ml of the aqueous liquid was sprayed onto the pan, using a conventional plastic spray bottle with a trigger sprayer. The second pan (pan #2) was sprayed 7 times in the same manner as pan #1, and with the same amount of the aqueous liquid, using the same four aqueous liquids, with the exception that the aqueous liquids had been "energized" using magnets about several minutes prior to their use in pan #2 ("energized" rubbing alcohol, mouthwash, wine or cola). After each pan was sprayed 7 times with the aqueous liquid, each pan was allowed to sit for 7 minutes with the motor oil and non-energized or "energized" liquid present thereon (to rest right side up upon a surface). At the conclusion of this 7-minute period, each pan was turned upside down on a surface to allow the motor oil and aqueous liquid to drain off of the pan via gravity onto the surface for 7 minutes. At the conclusion of the second 7-minute period, the pans were each returned right side up and rested on a surface. Then, the motor oil dispersion in each of the pans, and the difference in the motor oil dispersion between the two pans, was observed. As is described below, and as is shown in the figures, the difference in the motor oil dispersion between the two pans was very dramatic. In each of the figures that resulted from these tests, and that contain two pictures in the same figure, the pan to which a non-energized aqueous liquid was sprayed is shown on the left side, and the pan to which an "energized" aqueous liquid was sprayed is shown on the right side. Further, although rubbing alcohol, mouthwash, wine and cola are all vastly different aqueous liquids, when each is "energized," it reacts in a noticeably different manner when in contact with motor oil in comparison with when it is not "energized".

Test No. 1—Rubbing Alcohol

In this test, the aqueous liquid that was sprayed into the pans was 100% rubbing alcohol (in a non-energized form for pan #1, and in an "energized" form for pan #2). Rubbing alcohol has a water content of about 30%, which is the lowest water content of all of the aqueous liquids that were tested in this example.

Figure 24:
FIG. 24 is a photograph showing in Test No. 1 of Example 4: (a) non-stick cake pan #1 (left side) on its side just after it had been sprayed with 7 applications of 100% rubbing alcohol that had not been "energized"; and (b) non-stick cake pan #2 (right side) on its side just after it had been sprayed with 7 applications of 100% rubbing alcohol that had been "energized."

FIG. 24 is a photograph showing: (a) pan #1 (left side) on its side just after it had been sprayed with 7 applications of 100% rubbing alcohol that had not been "energized"; and (b) pan #2 (right side) on its side just after it had been sprayed with 7 applications of 100% rubbing alcohol that had been "energized." It can be seen that the motor oil is adhering to pan #1 (sticking to its surfaces), but not to pan #2. Also, it can be seen that, in comparison with pan #1 (non-energized rubbing alcohol), a significantly greater amount of motor oil has been removed from pan #2 ("energized" rubbing alcohol), and is present on the paper towel upon which it is resting. Significantly less motor oil can be seen on the paper towel upon which pan #1 is resting, which indicates that more of the motor oil is still present in the pan. From a comparison of pan #1 and pan #2 in FIG. 24, it can also clearly be seen that the "energized" rubbing alcohol mobilizes the motor oil (causes it to move) more rapidly and more completely than the non-energized rubbing alcohol, and that the surface tension of the motor oil has been affected to a greater extent by the "energized" rubbing alcohol in comparison with the non-energized rubbing alcohol.

Test No. 2—Mouth Wash

Figure 31:
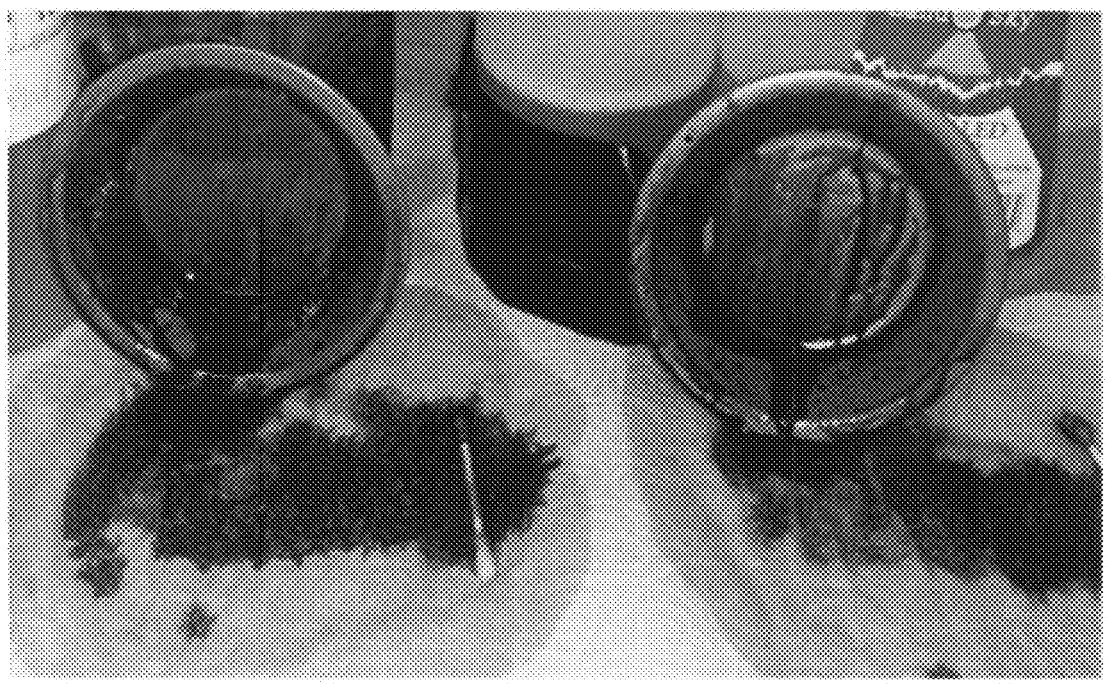
FIG. 31 is a photograph showing in Test No. 2 of Example 4 pan #1 (left side) and pan #2 (right side) at the conclusion of the test, and after an application of 10 mL of non-energized mouthwash had been sprayed onto pan #1, and an application of 10 mL of "energized" mouthwash had been sprayed onto pan #2.

In this test, the aqueous liquid that was sprayed into the pans was 100% mouthwash (in a non-energized form for pan #1, and in an "energized" form for pan #2). Mouthwash has a water content of about 78.1%. At the conclusion of this test, an application of 10 mL of non-energized mouthwash was sprayed onto pan #1, and an application of 10 mL of "energized" mouthwash was sprayed onto pan #2, both as rinsing agents (FIG. 31).

Figure 25:
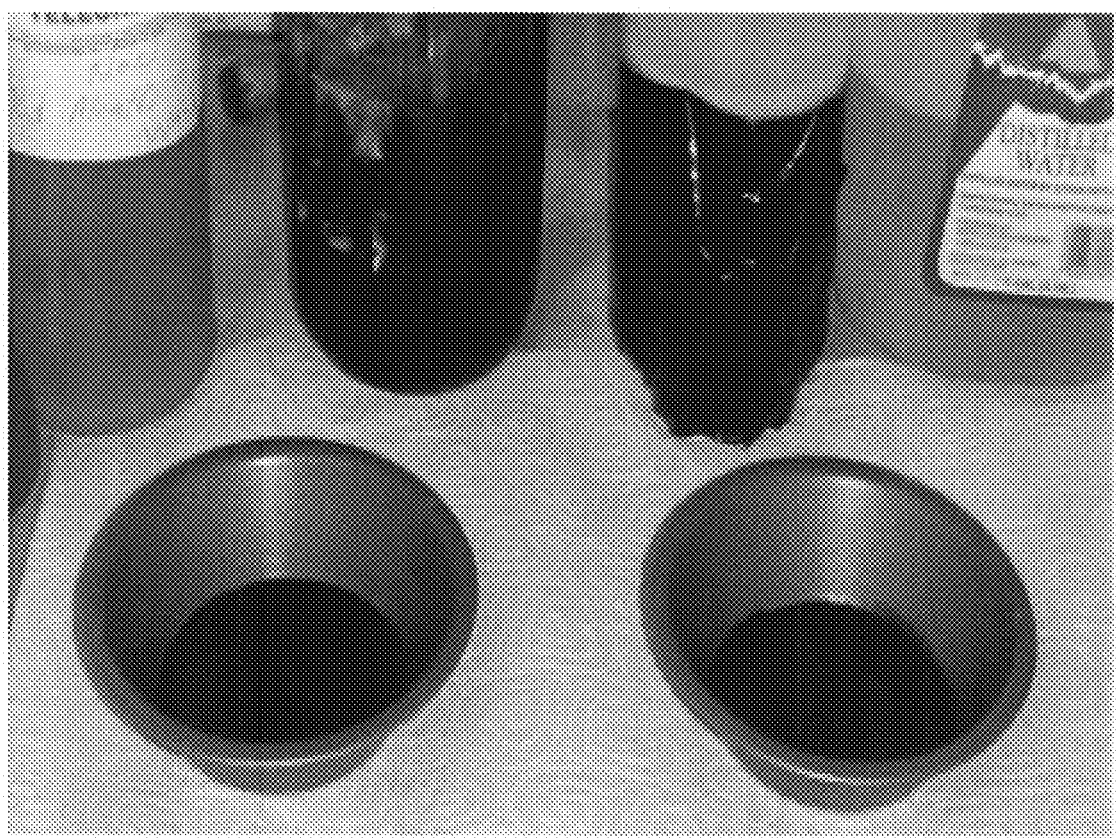
FIG. 25 is a photograph showing in Test No. 2 of Example 4 pan #1 (left side) and pan #2 (right side) after 3 mL of dirty motor oil was poured onto the bottom of each pan, and prior to spaying either pan with an aqueous liquid.

FIG. 25 is a photograph showing pan #1 (left side) and pan #2 (right side) after 3 mL of dirty motor oil was poured onto the bottom of each pan, and prior to spaying either pan with an aqueous liquid.

Figure 26:
FIG. 26 is a photograph showing in Test No. 2 of Example 4 one of the pans just after it had been sprayed with 7 applications of 100% mouthwash.

FIG. 26 is a photograph showing one of the pans just after it had been sprayed with 7 applications of 100% mouthwash.

Figure 27:
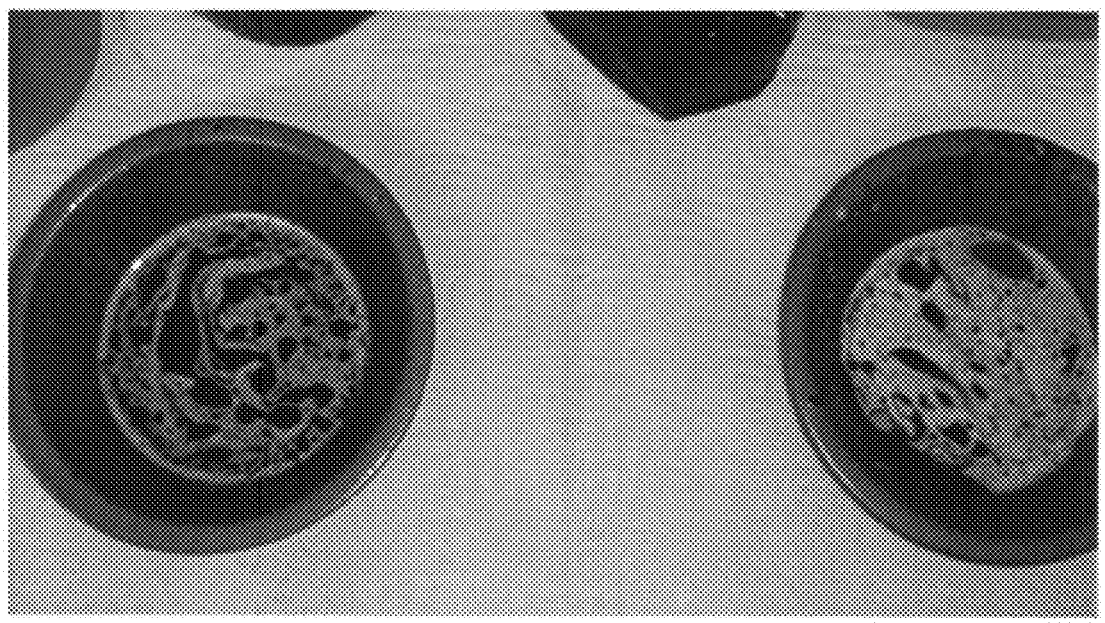
FIG. 27 is a photograph showing in Test No. 2 of Example 4 pan #1 (left side) and pan #2 (right side) sitting right side up on a counter after each pan had been allowed to sit for 7 minutes (after pan #1 had been sprayed with 7 applications of 100% mouthwash that had not been "energized", and pan #2 had been sprayed with 7 applications of 100% mouthwash that had been "energized"), with the dirty motor oil and non-energized or "energized" liquid present thereon.

FIG. 27 is a photograph showing pan #1 (left side) and pan #2 (right side) sitting right side up upon a counter after each pan had been allowed to sit for 7 minutes (after having been sprayed with 7 applications of 100% mouthwash) with the motor oil and non-energized or "energized" liquid present thereon. A significant difference between the motor oil and mouthwash mixture that is present in pan #1 and pan #2 can be seen. Pan #2 shows a significantly greater separation between the motor oil and the mouthwash in comparison with pan #1.

Figure 28:
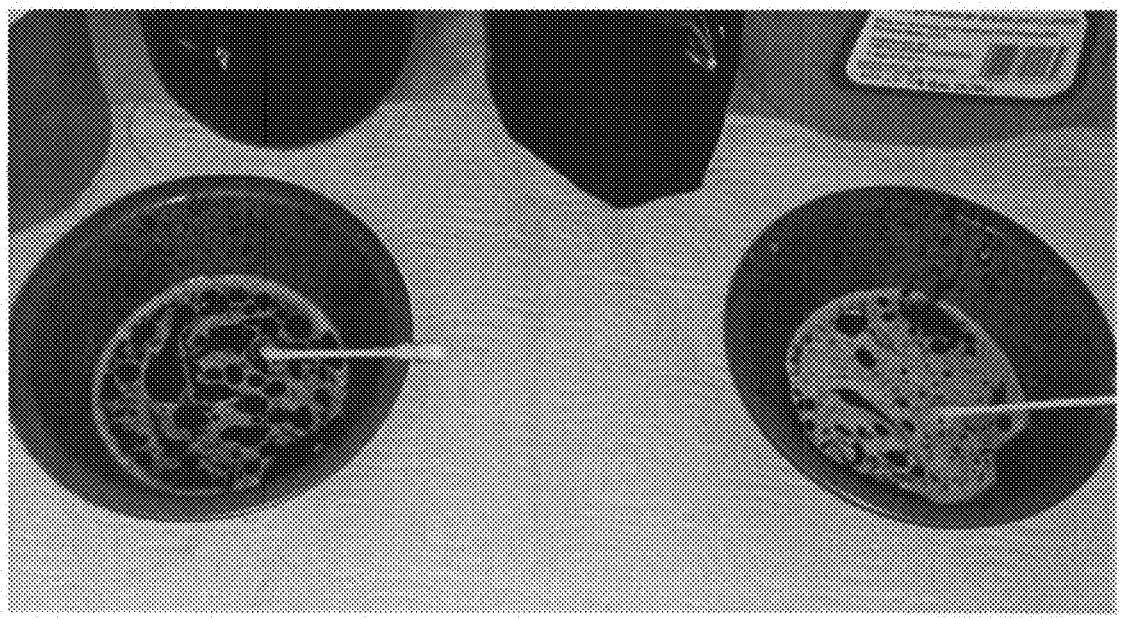
FIG. 28 is a photograph showing in Test No.2 of Example 4 pan #1 (left side) and pan #2 (right side) as they are present in FIG. 27, with the exception that the dirty motor oil and mouthwash mixtures are being agitated with cotton swabs.

FIG. 28 is a photograph showing pan #1 (left side) and pan #2 (right side) as they are present in FIG. 27, with the exception that the motor oil and mouthwash mixtures are being agitated with cotton swabs.

Figure 29:
FIG. 29 is a photograph showing in Test No. 2 of Example 4 pan #1 (left side) and pan #2 (right side) after they had been turned upside down on a paper towel resting on a counter, and permitted to sit for 7 minutes to allow the dirty motor oil and mouthwash to drain off of the pans via gravity onto the paper towel.

FIG. 29 is a photograph showing pan #1 (left side) and pan #2 (right side) after they had been turned upside down on a paper towel resting on a counter, and permitted to sit for 7 minutes to allow the motor oil and mouthwash to drain off of the pans via gravity onto the paper towel.

Figure 30:
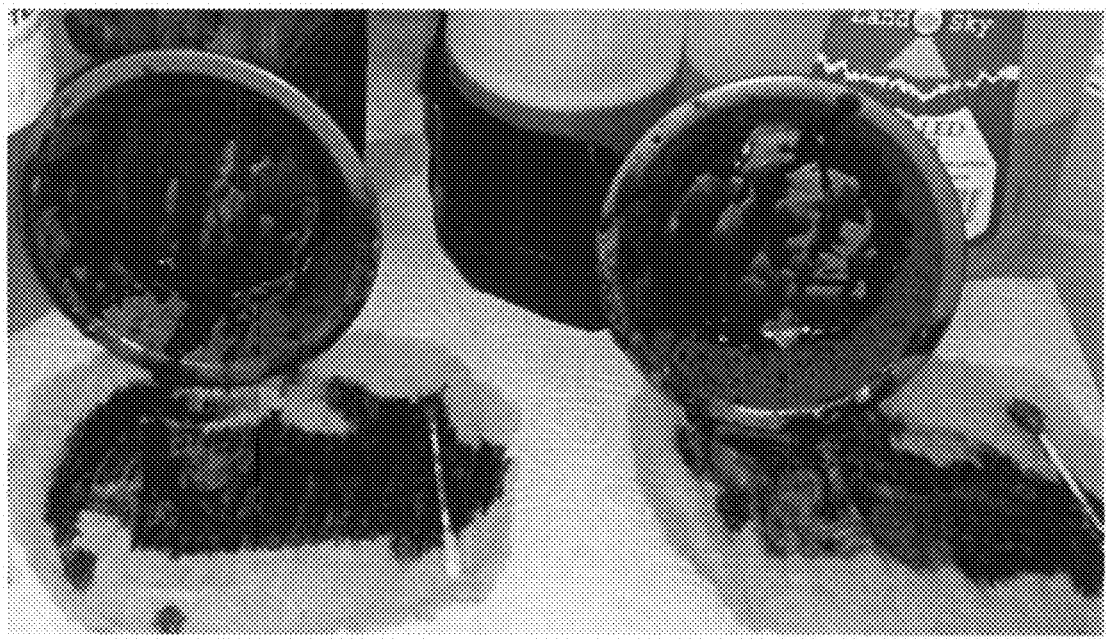
FIG. 30 is a photograph showing in Test No. 2 of Example 4 pan #1 (left side) and pan #2 (right side) after they had been turned onto their sides Oust after having sat for 7 minutes upside down on a paper towel).

FIG. 30 is a photograph showing pan #1 (left side) and pan #2 (right side) after they had been turned onto their sides 0ust after having sat for 7 minutes upside down on a paper towel). A visible difference can clearly be seen with respect to the adhesion of motor oil onto the surfaces of pan #1 (non-energized mouthwash) in connection with the adhesion of motor oil onto the surfaces of pan #2 ("energized" mouthwash). The adhesion of the motor oil to the surfaces of pan #1 was significantly greater in comparison with pan #2. Although the surface materials of both pans were the same, when an "energized" mouthwash was applied to the surfaces of pan #2, the motor oil readily removed itself from the surfaces, whereas when a non-energized mouthwash was applied to the surfaces of pan #1, the motor oil did not do so, but rather adhered to the surfaces. It is apparent that significantly more motor oil removed itself from pan #2 in comparison with pan #1. The bottom of pan #2 is more visible than the bottom of pan #1, and the motor oil has beaded on the sides of pan #2, unlike pan #1.

FIG. 31 shows pan #1 (left side) and pan #2 (right side) at the conclusion of this test, and after an application of 10 mL of non-energized mouthwash was sprayed onto pan #1, and an application of 10 mL of "energized" mouthwash was sprayed onto pan #2, both as rinsing agents. It can be seen that a significantly greater amount of motor oil remains clinging to the surfaces of pan #1 in comparison with the surfaces of pan #2. The bottom of pan #1 appears to be completely coated with motor oil, whereas the bottom of pan #2 has large areas that are not coated with motor oil (that appear to be clean).

\*\*\*

This same experiment was performed a second time in the exact same manner, with the exception that, at the conclusion of the test, the final application of 10 mL of mouthwash that was sprayed into pan #1 (in a non-energized form) and into pan #2 (in an "energized" form) as rinsing agents had been diluted with 3 ml of steam distilled water (the same water employed in Example 3), resulting in a mouthwash water mixture containing 70% mouthwash and 30% steam distilled water.

The "energized" rinsing agent (diluted mouthwash) showed a significantly more rapid rinsing and greater dispersion of the motor oil (pan #2) in comparison with the non-"energized" rinsing agent, as well as a much greater penetration of the motor oil through the white paper towel upon which the pans were sitting, which evidences the dispersing power of the "energized" rinsing agent. Further, a significantly higher volume of motor oil was removed from pan #2 ("energized" rinsing agent) in comparison with pan #2 (non-energized rinsing agent).

Test No. 3—Coca Cola

Figure 32:
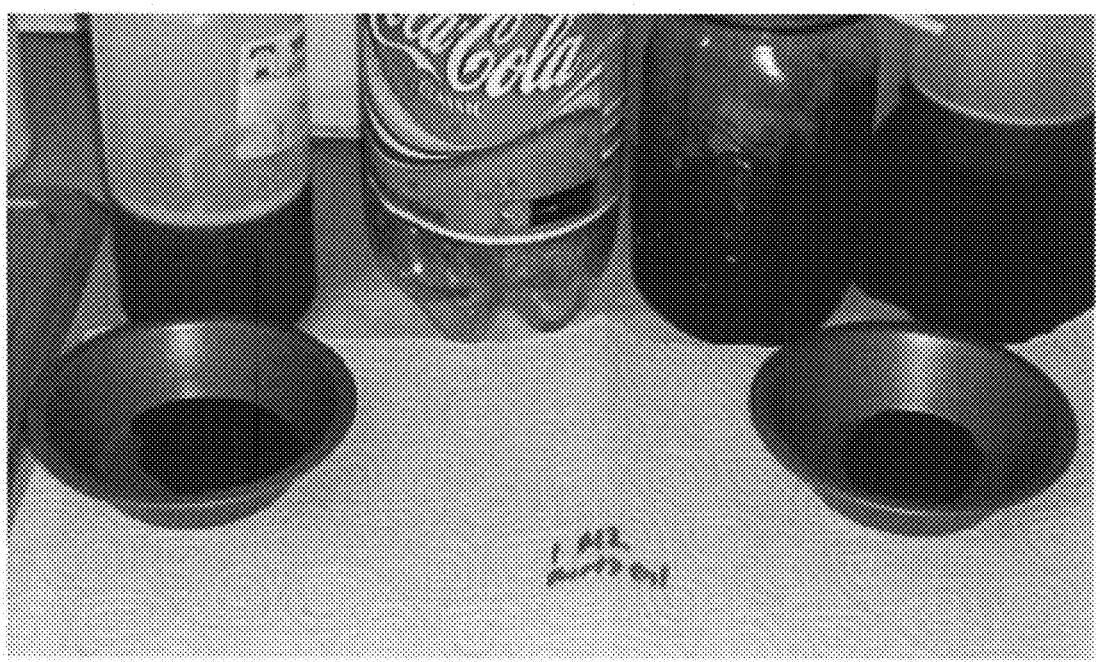
FIG. 32 is a photograph in Test No. 3 of Example 4 showing pan #1 (left side) and pan #2 (right side) after 3 mL of dirty motor oil was poured onto the bottom (upper surface) of each pan, and prior to spaying either pan with an aqueous liquid.
Figure 33:
FIG. 33 is a photograph showing in Test No. 3 of Example 4 one of the pans as the pan is being sprayed with 7 applications of 100% Coca Cola.
Figure 34:
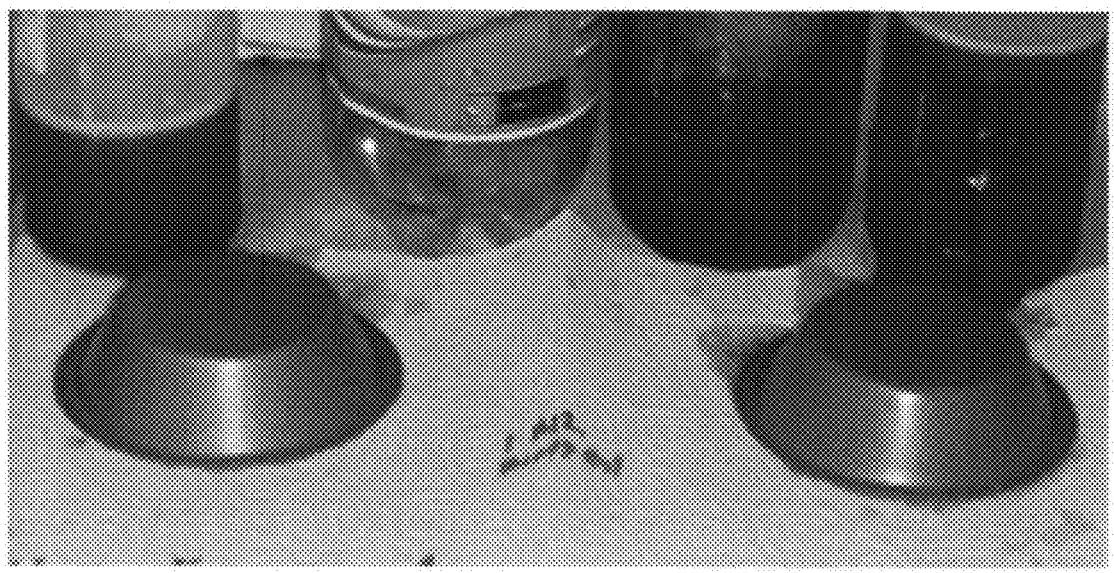
FIG. 34 is a photograph showing in Test No. 3 of Example 4 pan #1 (left side) and pan #2 (right side) after the pans were immediately turned upside down on a paper towel to drain for less than about 10 seconds (after having been sprayed with Coca Cola).

In this test, after 3 mL of dirty motor oil was poured onto the bottom of each pan (FIG. 32), 10 mL of 100% Coca Cola (as the aqueous liquid) was sprayed into the pans (in a non-energized form for pan #1, and in an "energized" form for pan #2). Coca Cola, the formulation of which is a trade secret, is believed to have a water content of about 70% or higher. (FIG. 33 is a photograph showing one of the pans being sprayed with 100% Coca Cola.) The pans were then immediately turned upside down onto a paper towel to drain for less than about 10 seconds (FIG. 34). Thereafter, both pans were placed onto their sides and allowed to drain for 3 minutes (FIG. 35).

Figure 35:
FIG. 35 is a photograph showing in Test No. 3 of Example 4 pan #1 (left side) and pan #2 (right side) after the pans were both placed onto their sides and allowed to drain for 3 minutes.

In FIG. 35, a significant difference can be seen regarding an adhesion of the motor oil onto the surfaces of the pan between pan #1 (non-energized Coca Cola) and pan #2 ("energized" Coca Cola). The dispersion of the motor oil is much greater for pan #2 in comparison with pan #1. Pan #2 has very little motor oil remaining on its sides (inner surfaces) in comparison with pan #1, and the motor oil that is present on the bottom (upper surface) of pan #1 appears to be much denser in comparison with pan #2.

Test No. 4—Zinfandel Wine

Figure 36:
FIG. 36 is a photograph in Test No. 4 of Example 4 showing pan #1 (left side) and pan #2 (right side) after 3 mL of dirty motor oil was poured onto the bottom (upper surface) of each pan, and prior to spaying either pan with an aqueous liquid.

In this test, after 3 mL of dirty motor oil was poured onto the bottom of each pan (FIG. 36), 10 mL of 100% Zinfandel wine (as the aqueous liquid) was sprayed into the pans (in a non-energized form for pan #1, and in an "energized" form for pan #2). Zinfandel wine has a water content of about 87%. The pans were then immediately turned upside down on a paper towel to drain for less than about 10 seconds. Thereafter, both pans were placed onto their sides and allowed to drain for 3 minutes (FIG. 37).

Figure 37:
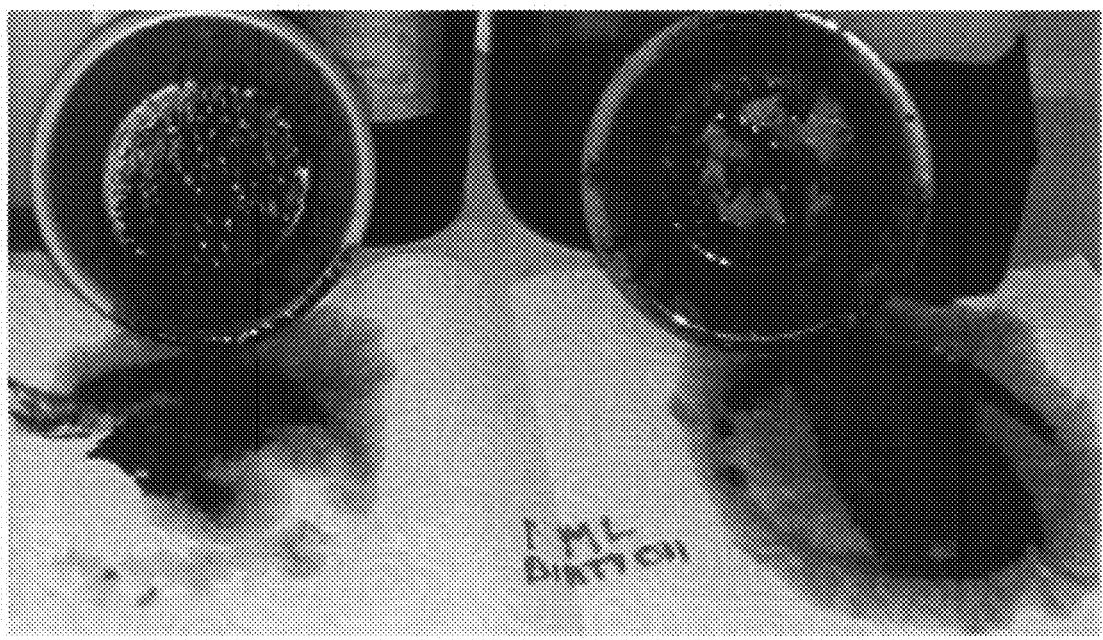
FIG. 37 is a photograph showing in Test No. 4 of Example 4 pan #1 (left side) and pan #2 (right side) after the pans were both placed onto their sides and allowed to drain for 3 minutes (after having been sprayed with Zinfandel wine, and turned upside down on a paper towel to drain for less than about 10 seconds).

In FIG. 37, a significant difference can be seen regarding an adhesion of the motor oil onto the surfaces of the pan between pan #1 (non-energized Zinfandel wine) and pan #2 ("energized" Zinfandel wine). The dispersion of the motor oil is much greater in connection with pan #2 in comparison with pan #1. The motor oil coating on the bottom (upper surface) of pan #1 appears to be much denser in comparison with pan #2. Also, in contrast with pan #1, clean areas (areas that do not contain motor oil) can be seen on the bottom (upper surface) of pan #2, and a significantly greater dispersion of Zinfandel wine and motor oil can be seen across the paper towel upon which pan #2 is sitting in comparison with the paper towel upon which pan #1 is sitting. It is clear from FIG. 37 that a significantly greater percentage of motor oil has dispersed from pan #2 in comparison with pan #1, which has a significantly larger quantity of motor oil remaining on the bottom (upper surface) of the pan.

EXAMPLE 5

Teeth Whitening—Les Washington

For about one year, starting just after a dental examination by his dentist, Marsha A. Gordon, DMD, P. C. (Dunwoody, Ga.), in November of 2005, Les Washington, of Dunwoody, Georgia, drank each day one bottle of 100% steam distilled Nursery water (DS Waters of America, Atlanta, Ga.) that had been "energized" 8 to 16 ounces at a time, 2 to 3 times per day, 3 to 4 days per week. No commercial or other treatments, other than brushing, were employed to whiten Mr. Washington's teeth during this one-year period of time. Each bottle of water consumed had first been "energized" using two magnets, each having a Gauss strength of 3500, which were placed upon opposite sides of the water bottle for less than 1 minute.

Figure 38:
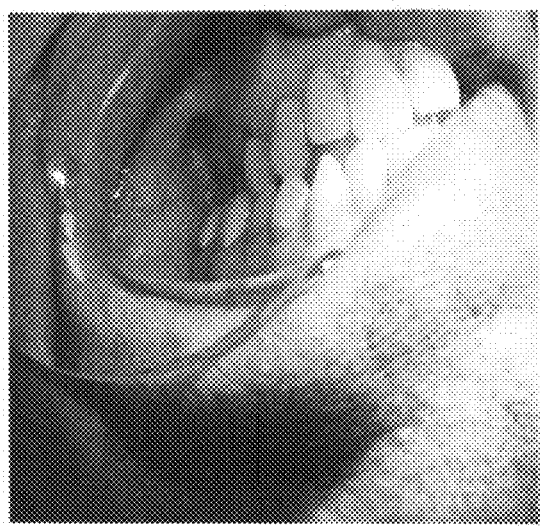
FIG. 38 is a series of two separate photographs showing in Example 5 the teeth of Les Washington at a dental examination just after finishing a one-year period of drinking "energized" steam distilled water on a daily basis.
Figure 38:
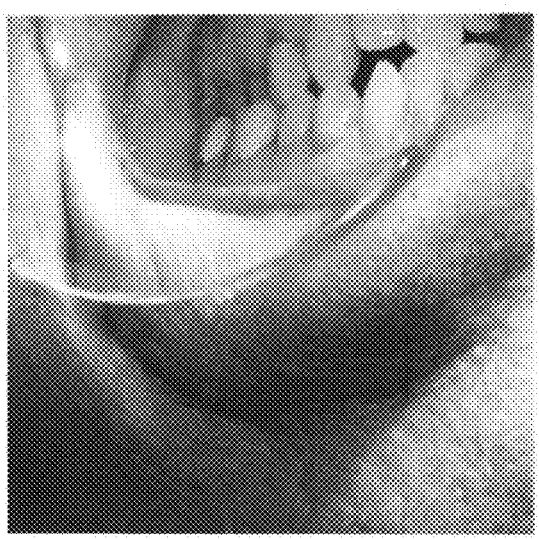

At the conclusion of the one-year period of time, Mr. Washington underwent another dental examination by Dr. Gordon, who informed him that his teeth were now significantly whiter than they had been at his dental examination approximately one year earlier, and took two photographs of his teeth. In fact, his teeth were whiter than some crowns that had been present in his mouth, the color of which had been matched to the color of his teeth at the time that they had been inserted into his mouth, which was prior to his drinking "energized" steam distilled water. In a letter dated Nov. 17, 2006, Dr. Gordon documented these results by stating, "Enclosed photos that show that your teeth are whiter now than your crowns. The whitener that you have been using has lightened your teeth." The photographs that Dr. Gordon referred to in her letter are shown in FIG. 38.

EXAMPLE 6

Teeth Whitening—Dr. Bill Pope

For about six weeks starting in the middle of December of 2006, Dr. Bill Pope of Marietta, Georgia, drank 100% water (in bottles) on a daily basis, some of which had been "energized," and some of which had not, according to the following schedule:
  (a) 20 ounces of "energized" water five days per week (Monday—Friday); and
  (b) 20 ounces of mineral enhanced water (Disani bottled water) that was not "energized" two days per week (Saturday—Sunday).

The bottles of water were "energized" in the same manner that is described in Example 5.

In late January 2007, after six weeks of the above regiment, Dr. Pope had a regularly scheduled (every six months) dentist appointment with dentist, Dr. Barry Smith, Marietta, Ga. During this appointment for x-rays and cleaning, the hygienist without any prompting said, "You don't drink much tea or coffee do you." Dr. Pope informed the hygienist that he does not drink coffee, but drinks tea several times per week. She asked Dr. Pope if he was using Crest Whitestrips, and he informed her that he was not using any whitening substance. She then informed Dr. Pope that his teeth didn't show any sign of staining, and that his gums were healthy.

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this document, various books, patents, journal articles, web sites and other publications have been cited. The entireties of each of these books, patents, journal articles, web sites and other publications are hereby incorporated by reference herein.

What is claimed is:

1. A method for increasing an effectiveness of an aqueous or non-aqueous cleaning composition that is to be diluted with water, or with another aqueous composition, prior to use comprising:
   (a) "energizing" just prior to use at a temperature and pressure, and for a period of time, that are effective for such "energizing," a portion or all of the water, or other aqueous composition, that is employed to dilute the cleaning composition by positioning one or more magnets having a combined Gauss strength ranging from about 100 to about 10,000 Gauss in a manner in relation to the water, or other aqueous composition, that one or more magnetic forces or magnetic fields are created on or over the water, or other aqueous composition; and
   (b) diluting the cleaning composition with the "energized" water, or other aqueous composition;
wherein the cleaning composition becomes effective at a dilution ratio of water, or other aqueous composition, to cleaning composition ranging from about 1:10 to about 10:1; wherein the diluted cleaning composition exhibits an enhanced effectiveness for cleaning one or more objects or surfaces in comparison with the same diluted cleaning composition that does not include "energized" water, or another aqueous composition;
wherein the diluted cleaning composition has an ability to exhibit the enhanced activity in the absence of an electrical current; and
wherein if more than one magnet is employed, the magnets do not need to be positioned in any particular manner with respect to their polarities.

2. The method of claim 1, wherein the cleaning composition is also "energized," and wherein the cleaning composition is "energized" in the same manner that the water, or other aqueous composition, is "energized ".

3. The method of claim 1, wherein the method does not include any vortex flow or other circulation of the water, or other aqueous composition.

4. The method of claim 1, wherein none of the "energized" water, or other aqueous composition, is stored in a holding container prior to use.

5. The method of claim 1, wherein an electrical or current conductor is not employed.

6. The method of claim 1, wherein only one magnet is employed.

7. The method of claim 1, wherein two magnets are employed, and wherein the N or S poles, or both, of one magnet are not aligned with, or positioned towards, or opposite to, the N or S poles, or both, of the other magnet.

8. The method of claim 1, wherein the water, or other aqueous composition, is "energized" during use.

9. The method of claim 1, wherein the water, or other aqueous composition, is "energized" at the point of use.

10. The method of claim 1, wherein the water, or other aqueous composition, is "energized" less than about 30 seconds prior to its use.

11. The method of claim 1, wherein the water, or other aqueous composition, is "energized" less than about 1 minute prior to its use.

12. The method of claim 1, wherein the water, or other aqueous composition, is "energized" less than about 3 minutes prior to its use.

13. The method of claim 1, wherein the water, or other aqueous composition, is "energized" less than about 7 minutes prior to its use.

14. The method of claim 1, wherein water is employed.

15. The method of claim 14, wherein the water is steamed distilled water.

16. The method of claim 14, wherein the water is nursery water.

17. The method of claim 1, wherein the one or more magnets have a combined Gauss strength ranging from about 200 to about 9,000 Gauss.

18. The method of claim 17, wherein the one or more magnets have a combined Gauss strength ranging from about 500 to about 8,000 Gauss.

19. The method of claim 18 wherein the one or more magnets have a combined Gauss strength ranging from about 800 to about 7,000 Gauss.

20. The method of claim 19, wherein the one or more magnets have a combined Gauss strength ranging from about 1,000 to about 6,000 Gauss.

21. The method of claim 20, wherein the one or more magnets have a combined Gauss strength ranging from about 1,500 to about 5,500 Gauss.

22. The method of claim 21, wherein the one or more magnets have a combined Gauss strength ranging from about 2,000 to about 5,000 Gauss.

23. The method of claim 22, wherein the one or more magnets have a combined Gauss strength ranging from about 3,000 to about 4,000 Gauss.

24. The method of claim 23, wherein the one or more magnets have a combined Gauss strength ranging from about 3,500 to about 4,000 Gauss.

25. The method of claim 24, wherein the one or more magnets have a combined Gauss strength ranging from about 1500 to about 3500.

26. A cleaning composition that is effective for cleaning one or more objects or surfaces comprising a cleaning composition that has been "energized" in the manner that is described in claim 1.

27. The cleaning composition of claim 26 wherein the one or more magnets have a combined Gauss strength ranging from about 100 to about 4,900.

28. The cleaning composition of claim 27, wherein the one or more magnets have a combined Gauss strength ranging from about 100 to about 3,000.

29. The cleaning composition of claim 28, wherein the one or more magnets have a combined Gauss strength ranging from about 100 to about 1,500.

30. The cleaning composition of claim 29, wherein the one or more magnets have a combined Gauss strength ranging from about 100 to about 500.

31. The method of claim 1, wherein the one or more magnets have a combined Gauss strength ranging from about 100 to about 4,900.

32. The method of claim 31, wherein the one or more magnets have a combined Gauss strength ranging from about 100 to about 3,000.

33. The method of claim 32, wherein the one or more magnets have a combined Gauss strength ranging from about 100 to about 1,500.

34. The method of claim 33, wherein the one or more magnets have a combined Gauss strength ranging from about 100 to about 500.

35. A method for increasing an effectiveness of an aqueous or non-aqueous cleaning composition that is to be diluted with water, or with another aqueous composition, prior to use comprising:
(a) "energizing" just prior to use at a temperature and pressure, and for a period of time, that are effective for such "energizing," a portion or all of the cleaning composition by positioning one or more magnets having a combined Gauss strength ranging from about 100 to about 10,000 Gauss in a manner in relation to the cleaning composition that one or more magnetic forces or magnetic fields are created on or over the cleaning composition; and
(b) diluting the cleaning composition with the water, or other aqueous composition, wherein the water or other aqueous composition is, optionally, also "energized" just prior to use at a temperature and pressure, and for a period of time, that are effective for such "energizing," a portion or all of the water, or other aqueous composition, by positioning one or more magnets having a combined Gauss strength ranging from about 100 to about 10,000 Gauss in a manner in relation to the water, or other aqueous composition, that one or more magnetic forces or magnetic fields are created on or over the water, or other aqueous composition;
wherein the cleaning composition becomes effective at a dilution ratio of water, or other aqueous composition, to cleaning composition ranging from about 1:10 to about 10:1;
wherein the diluted cleaning composition exhibits an enhanced activity or effectiveness for cleaning one or more objects or surfaces in comparison with the same diluted cleaning composition that does not include "energized" cleaning solution, water or other aqueous composition;
wherein the diluted cleaning composition has an ability to exhibit the enhanced activity in the absence of an electrical current; and
wherein if more than one magnet is employed, the magnets do not need to be positioned in any particular manner with respect to their polarities.

36. A cleaning composition that is effective for cleaning one or more objects or surfaces comprising a cleaning composition that has been "energized" in the manner that is described in claim 35.

37. The cleaning composition of claim 36 wherein the one or more magnets have a combined Gauss strength ranging from about 100 to about 4,900.

38. The cleaning composition of claim 37, wherein the one or more magnets have a combined Gauss strength ranging from about 100 to about 3,000.

39. The cleaning composition of claim 38, wherein the one or more magnets have a combined Gauss strength ranging from about 100 to about 1,500.

40. The cleaning composition of claim 39, wherein the one or more magnets have a combined Gauss strength ranging from about 100 to about 500.

41. The method of claim 35, wherein the one or more magnets have a combined Gauss strength ranging from about 100 to about 4,900.

42. The method of claim 41, wherein the one or more magnets have a combined Gauss strength ranging from about 100 to about 3,000.

43. The method of claim 42, wherein the one or more magnets have a combined Gauss strength ranging from about 100 to about 1,500.

44. The method of claim 43, wherein the one or more magnets have a combined Gauss strength ranging from about 100 to about 500.

* * * * *